United States Patent
Sjolund

(10) Patent No.: US 11,996,178 B2
(45) Date of Patent: May 28, 2024

(54) PARAMETER SEARCH IN RADIOTHERAPY TREATMENT PLAN OPTIMIZATION

(71) Applicant: Elekta AB (publ), Stockholm (SE)

(72) Inventor: Jens Olof Sjolund, Stockholm (SE)

(73) Assignee: Elekta AB (publ), Stockholm (SE)

( * ) Notice: Subject to any disclaimer, the term of this patent is extended or adjusted under 35 U.S.C. 154(b) by 170 days.

(21) Appl. No.: 17/248,670

(22) Filed: Feb. 2, 2021

(65) Prior Publication Data

US 2021/0158929 A1  May 27, 2021

Related U.S. Application Data

(63) Continuation-in-part of application No. 16/512,972, filed on Jul. 16, 2019, now Pat. No. 11,605,452.

(51) Int. Cl.
*G16H 20/40* (2018.01)
*A61N 5/10* (2006.01)
(Continued)

(52) U.S. Cl.
CPC ........... *G16H 20/40* (2018.01); *A61N 5/1031* (2013.01); *A61N 5/1038* (2013.01);
(Continued)

(58) Field of Classification Search
CPC ........ G16H 20/40; G16H 30/40; G16H 50/20; G16H 50/50; G16H 50/70; G16H 10/60;
(Continued)

(56) References Cited

U.S. PATENT DOCUMENTS

| 11,367,520 B2 | 6/2022 | Sjölund |
| 11,605,452 B2 | 3/2023 | Adler et al. |

(Continued)

FOREIGN PATENT DOCUMENTS

| AU | 2020312643 | 7/2023 |
| CN | 114375216 | 4/2022 |

(Continued)

OTHER PUBLICATIONS

"U.S. Appl. No. 16/512,962, Response filed Jul. 13, 2021 to Non-Final Office Action dated Apr. 13, 2021", 18 pages.
(Continued)

*Primary Examiner* — Robert W Morgan
*Assistant Examiner* — Liza Tony Kanaan
(74) *Attorney, Agent, or Firm* — Schwegman Lundberg & Woessner, P.A.

(57) ABSTRACT

Techniques for generating a radiotherapy treatment plan are provided. The techniques include receiving a radiotherapy optimization problem, the radiotherapy problem comprising a plurality of parameters; processing the radiotherapy optimization problem to instantiate a first set of candidate parameters; converting the first set of candidate parameters into an adapted representation; defining an adapted radiotherapy optimization problem as a function of the adapted representation such that a given solution to the adapted optimization problem estimates a solution to the radiotherapy optimization problem; processing the adapted radiotherapy optimization problem to estimate a function of the solution to the adapted radiotherapy optimization problem; and processing the estimated function of the solution to the adapted optimization problem to generate a deliverable radiotherapy treatment plan.

37 Claims, 8 Drawing Sheets

(51) Int. Cl.
| | |
|---|---|
| *G06N 3/08* | (2023.01) |
| *G16H 30/40* | (2018.01) |
| *G16H 50/20* | (2018.01) |
| *G16H 50/50* | (2018.01) |
| *G16H 50/70* | (2018.01) |

(52) U.S. Cl.
CPC .............. *A61N 5/1039* (2013.01); *G06N 3/08* (2013.01); *G16H 30/40* (2018.01); *G16H 50/20* (2018.01); *G16H 50/50* (2018.01); *G16H 50/70* (2018.01); *A61N 2005/1032* (2013.01); *A61N 2005/1035* (2013.01)

(58) Field of Classification Search
CPC .. A61N 5/1031; A61N 5/1038; A61N 5/1039; A61N 2005/1032; A61N 2005/1035; A61N 2005/1041; G06N 3/08; G06N 3/0454; G06N 5/003
See application file for complete search history.

(56) References Cited

U.S. PATENT DOCUMENTS

| | | | |
|---|---|---|---|
| 2004/0165696 | A1 | 8/2004 | Lee |
| 2006/0256915 | A1 | 11/2006 | Otto et al. |
| 2012/0059779 | A1 | 3/2012 | Syed et al. |
| 2017/0177812 | A1* | 6/2017 | Sjölund .................. G16H 20/40 |
| 2017/0303813 | A1* | 10/2017 | Lattanzi ................. G01R 33/56 |
| 2018/0221685 | A1 | 8/2018 | Eriksson |
| 2018/0315188 | A1 | 11/2018 | Tegzes et al. |
| 2019/0074079 | A1* | 3/2019 | Zankowski ........ G06V 10/7796 |
| 2019/0209867 | A1 | 7/2019 | Sun et al. |
| 2019/0333623 | A1* | 10/2019 | Hibbard ................... G06N 3/08 |
| 2020/0104695 | A1* | 4/2020 | Laaksonen ............. G16H 50/70 |
| 2020/0169085 | A1 | 5/2020 | Becher et al. |
| 2020/0261744 | A1 | 8/2020 | Kumar et al. |
| 2020/0289847 | A1 | 9/2020 | Sjölund et al. |
| 2021/0020296 | A1 | 1/2021 | Sjölund |
| 2021/0020297 | A1 | 1/2021 | Adler et al. |

FOREIGN PATENT DOCUMENTS

| | | | |
|---|---|---|---|
| CN | 114401768 | 4/2022 | |
| WO | 2015103184 | 7/2015 | |
| WO | WO-2015103184 A1 * | 7/2015 | ........... A61B 5/0036 |
| WO | 2019027924 | 2/2019 | |
| WO | 2019084547 | 5/2019 | |
| WO | WO-2021009056 A1 | 1/2021 | |
| WO | WO-2021009058 A1 | 1/2021 | |

OTHER PUBLICATIONS

"U.S. Appl. No. 16/512,962, Final Office Action dated Sep. 28, 2021", 30 pages.
"U.S. Appl. No. 16/512,972, Non Final Office Action dated Sep. 28, 2021", 19 pages.
"International Application Serial No. PCT/EP2020/069585, International Search Report dated Oct. 7, 2020", 5 pgs.
"International Application Serial No. PCT/EP2020/069585, Written Opinion dated Oct. 7, 2020", 6 pgs.
"International Application Serial No. PCT/EP2020/069588, International Search Report dated Oct. 14, 2020", 5 pgs.
"International Application Serial No. PCT/EP2020/069588, Written Opinion dated Oct. 14, 2020", 6 pgs.
Banert, Sebastian, et al., "Data-driven nonsmooth optimization", SIAM Journal on Optimization 30.1, (2020), 102-131.
Fine, Shai, et al., "Efficient SVM training using low-rank kernel representations", Journal of Machine Learning Research 2.Dec, (2001), 243-264.
Garnett, R., "Lecture 11: Bayesian Quadrature", University Lecture, [Online]. Retrieved from the Internet: <https://www.cse.wustl.edu/~garnett/cse515t/spring_2017/files/lecture_notes/11.pdf>, (2018), 4 pgs.

Provost, Serge B., et al., "The exact distribution of indefinite quadratic forms in noncentral normal vectors", Annals of the Institute of Statistical Mathematics 48.2, (1996), 381-394.
Rodriguez-Lujan, Irene, et al., "Quadratic programming feature selection", Journal of Machine Learning Research, (Apr. 2010), 26 pgs.
Sjolund, Jens, et al., "A linear programming approach to inverse planning in Gamma Knife radiosurgery", Medical physics 46.4, (2019), 1533-1544.
Zaheer, Manzil, et al., "Deep sets", Advances in neural information processing systems, (2017), 11 pgs.
U.S. Appl. No. 16/512,962, filed Jul. 16, 2019, Compressing Radiotherapy Treatment Plan Optimization Problems.
U.S. Appl. No. 16/512,972, filed Jul. 16, 2019, Radiotherapy Treatment Plan Optimization Using Machine Learning.
"U.S. Appl. No. 16/512,962, Notice of Allowance dated Mar. 4, 2022", 10 pgs.
"U.S. Appl. No. 16/512,972, Response filed Mar. 16, 2022 to Final Office Action dated Jan. 20, 2022", 12 pgs.
"U.S. Appl. No. 16/512,972, Advisory Action dated Mar. 28, 2022", 3 pgs.
"U.S. Appl. No. 16/512,972, Non Final Office Action dated Apr. 13, 2022", 28 pgs.
"U.S. Appl. No. 16/512,962, PTO Response to Rule 312 Communication dated Apr. 19, 2022", 2 pgs.
"U.S. Appl. No. 16/512,962, Amendment under CFR 1.312 filed Apr. 7, 2022", 3 pgs.
"International Application Serial No. PCT EP2022 052412, International Search Report dated May 6, 2022", 5 pgs.
"International Application Serial No. PCT EP2022 052412, Written Opinion dated May 6, 2022", 6 pgs.
"U.S. Appl. No. 16/512,962, Response filed Nov. 29, 2021 to Final Office Action dated Sep. 28, 2021", 14 pgs.
"U.S. Appl. No. 16/512,972, Response filed Dec. 20, 2021 to Non Final Office Action dated Sep. 28, 2021", 11 pgs.
"U.S. Appl. No. 16/512,962, Advisory Action dated Jan. 10, 2022", 4 pgs.
"U.S. Appl. No. 16/512,962, Examiner Interview Summary dated Jan. 18, 2022", 3 pgs.
"U.S. Appl. No. 16/512,972, Final Office Action dated Jan. 20, 2022", 21 pgs.
"U.S. Appl. No. 16/512,962, Response filed Jan. 27, 2022 to Advisory Action dated Jan. 10, 2022", 15 pgs.
"International Application Serial No. PCT EP2020 069585, International Preliminary Report on Patentability dated Jan. 27, 2022", 8 pgs.
"U.S. Appl. No. 16/512,972, Response filed Jul. 13, 2022 to Non Final Office Action dated Apr. 13, 2022", 13 pgs.
"U.S. Appl. No. 16/512,972, Examiner Interview Summary dated Jul. 19, 2022", 2 pgs.
"European Application Serial No. 20739661.5, Response to Communication pursuant to Rules 161 and 162 filed Jul. 18, 2022", 16 pgs.
"European Application Serial No. 20739662.3, Response to Communication pursuant to Rules 161 and 162 filed Aug. 24, 2022", 5 pgs.
"U.S. Appl. No. 16/512,962, Non Final Office Action dated Apr. 13, 2021", 28 pgs.
"Japanese Application Serial No. 2022-502892, Notification of Reasons for Refusal dated Dec. 27, 2022", w English Translation, 11 pgs.
"U.S. Appl. No. 16/512,972, Corrected Notice of Allowability dated Feb. 10, 2023", 7 pgs.
"Australian Application Serial No. 2020312643, First Examination Report dated Feb. 20, 2023", 3 pgs.
"Australian Application Serial No. 2020315113, First Examination Report Received dated Mar. 3, 2023", 3 pgs.
"U.S. Appl. No. 16/512,972, Notice of Allowance dated Nov. 7, 2022", 10 pgs.
"Japanese Application Serial No. 2022-502922, Notification of Reasons for Refusal dated Dec. 20, 2022", w English Translation, 7 pgs.

(56) References Cited

OTHER PUBLICATIONS

"Australian Application Serial No. 2020312643, Response filed Jun. 23, 2023 to First Examination Report dated Feb. 20, 2023", 39 pgs.

"Japanese Application Serial No. 2022-502892, Examiners Decision of Final Refusal dated Aug. 8, 2023", w o English Translation, 1 pg.

"Japanese Application Serial No. 2022-502922, Examiners Decision of Final Refusal dated Aug. 8, 2023", w o English Translation, 1 pg.

"International Application Serial No. PCT EP2022 052412, International Preliminary Report on Patentability dated Aug. 17, 2023", 8 pgs.

"Australian Application Serial No. 2020315113, Response filed Dec. 15, 2023 to First Examination Report Received dated Mar. 3, 2023", 23 pgs.

\* cited by examiner

PARAMETER SEARCH IN RADIOTHERAPY TREATMENT PLAN OPTIMIZATION

CLAIM FOR PRIORITY

This application is a continuation-in-part application of U.S. application Ser. No. 16/512,972, filed Jul. 16, 2019, which is hereby incorporated by reference in its entirety.

TECHNICAL FIELD

This disclosure relates generally to radiation therapy or radiotherapy optimization problems.

BACKGROUND

Radiotherapy is used to treat cancers and other ailments in mammalian (e.g., human and animal) tissue. The direction and shape of the radiation beam should be accurately controlled to ensure the tumor receives the prescribed radiation, and the placement of the beam should be such as to minimize damage to the surrounding healthy tissue (often called the organ(s) at risk (OARs)). Treatment planning can be used to control radiation beam parameters, and a radiotherapy device effectuates a treatment by delivering a spatially varying dose distribution to the patient.

Traditionally, for each patient, a radiation therapy treatment plan ("treatment plan") may be created using an optimization technique based on clinical and dosimetric objectives and constraints (e.g., the maximum, minimum, and mean doses to the tumor and critical organs). The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH) objectives), taking into account their individual importance (e.g., weighting) in order to produce a treatment plan which is clinically acceptable. This task can be a time-consuming, trial-and-error process that is complicated by the various OARs, because as the number of OARs increases (e.g., 21 are commonly segmented in a head-and-neck treatment), so does the complexity of the process. OARs distant from a tumor may be easily spared from radiation, while OARs close to or overlapping a target tumor may be difficult to spare.

Segmentation may be performed to identify the OARs and the area to be treated (for example, a planning target volume (PTV)). After segmentation, a dose plan may be created for the patient indicating the desirable amount of radiation to be received by the one or more PTV (e.g., target) and/or the OARs. A PTV may have an irregular volume and may be unique as to its size, shape, and position. A treatment plan can be calculated after optimizing a large number of plan parameters to ensure that enough dose is provided to the PTV(s) while as low a dose as possible is provided to surrounding healthy tissue. Therefore, a radiation therapy treatment plan may be determined by balancing efficient control of the dose to treat the tumor against sparing any OAR. Typically, the quality of a radiation treatment plan may depend upon the level of experience of the planner. Further complications may be caused by anatomical variations between patients.

OVERVIEW

In some embodiments, a computer-implemented method, non-transitory computer readable medium, and a system comprising a memory and processor are provided for generating a radiotherapy treatment plan. The computer-implemented method, non-transitory computer readable medium, and system perform operations that include: receiving, by processor circuitry, a radiotherapy optimization problem, the radiotherapy optimization problem comprising a plurality of parameters; processing the radiotherapy optimization problem to instantiate a first set of candidate parameters; converting the first set of candidate parameters into an adapted representation; defining an adapted radiotherapy optimization problem as a function of the adapted representation such that a given solution to the adapted radiotherapy optimization problem estimates a solution to the radiotherapy optimization problem; processing the adapted radiotherapy optimization problem to estimate a function of the solution to the adapted radiotherapy optimization problem; and processing the estimated function of the solution to the adapted radiotherapy optimization problem to generate a deliverable radiotherapy treatment plan.

In some aspects, instantiating the first set of candidate parameters comprises a sampling process that generates candidate parameters according to at least one of a deterministic pattern and a probability distribution.

In some aspects, the sampling process is adapted based on at least one of user input or the radiotherapy optimization problem.

In some aspects, the method includes processing at least one of the radiotherapy optimization problem, previously generated candidate parameters and the function of the solution to the adapted radiotherapy optimization problem to generate a new set of candidate parameters.

In some aspects, the new set of candidate parameters are generated according to a parameter search optimization problem comprising a bilevel optimization problem.

In some aspects, the parameter search optimization problem is solved using a learned or non-learned optimization process including at least one of a machine learning model, a simplex method, an interior point method, a Newton method, a quasi-Newton method, a Gauss-Newton method, a Levenberg-Marquardt method, a linear least-squares method, a gradient descent method, a projected gradient method, a conjugate gradient method, an augmented Lagrangian method, a Nelder-Mead method, a branch and bound method, a cutting plane method, simulated annealing, or sequential quadratic programming.

In some aspects, the adapted representation is at least one of a tensor representation, a canonical form of the radiotherapy optimization problem, or a representation of the radiotherapy optimization problem by an algebraic modeling language.

In some aspects, the adapted radiotherapy optimization problem is processed by a machine learning model comprising a deep neural network, a convolutional neural network or a graph neural network.

In some aspects, the processing of the adapted radiotherapy optimization problem to estimate the function of the solution to the adapted radiotherapy optimization problem comprises at least one of a (i) a surrogate function, (ii) upper and lower bounds, (iii) an optimization solver halted before convergence, (iv) interpolation of already obtained results, or (v) a trained machine learning model.

In some aspects, the function of the solution to the adapted optimization problem comprises at least one of (i) the solution itself, (ii) a resulting dose distribution or dose-based metrics such as dose volume histogram (DVH) criteria, (iii) radiobiological effects, (iv) radiosurgical metrics such as coverage, selectivity or gradient index, (v) metrics quantifying a complexity of radiotherapy delivery, (vi) geometrical deviations, or (vii) sensitivity to uncertainties.

In some aspects, processing the estimated solution to generate a deliverable solution comprises solving the radiotherapy optimization problem exactly using the corresponding set of candidate parameters.

In some aspects, the method includes converting the function of the solution to the adapted radiotherapy optimization problem from a multi-dimensional tensor to a set of scalars.

In some aspects, the radiotherapy optimization problem comprises at least one of images of a patient or patient volume, a segmentation of the patient volume, a dose kernel, a dose volume histogram constraint, or a dose constraint.

In some aspects, the first set of candidate parameters are converted into an adapted representation based on an affine function.

In some aspects, converting the first set of candidate parameters into an adapted representation comprises mapping organ-specific parameters to voxel-specific parameters structured in a multi-dimensional grid corresponding to a patient geometry.

In some aspects, the first set of candidate parameters comprise weights and reference doses for each structure in a set of structures, further comprising converting the first set of candidate parameters into a tensor representation by mapping the weights and reference doses to a tensor defined on a voxel grid and concatenating the tensor with dose maps defined on the same voxel grid.

In some aspects, processing the adapted radiotherapy optimization problem to estimate the function of the solution to the adapted radiotherapy optimization problem is performed in parallel or asynchronously.

In some aspects, the plurality of parameters are processed based on user input or automatically using an open-loop or closed-loop process.

In some aspects, the radiotherapy optimization problem is defined as:

$$x^*(w_S, \hat{d}_S) = \underset{x \in \Omega}{\mathrm{argmin}}\, g(x) + \sum_{S \in M} w_S \sum_{v \in S} f_S(\varphi_v^T x - \hat{d}_S)$$

where $x^* \in \Omega$ is a solution of the radiotherapy optimization problem, $\Omega$ is the feasible set, $w_S$ is a vector of weights for each structure S, $\varphi_v^T$ is a linear map of x to dose in a voxel v, $\hat{d}_S$ is a reference dose for structure S, and $g(x)$ and $f_S(x)$ are real-valued functions.

In some aspects, a computing apparatus includes: a processor; and a memory storing instructions that, when executed by the processor, configure the apparatus to: receive a radiotherapy optimization problem, the radiotherapy problem comprising a plurality of parameters; process the radiotherapy optimization problem to instantiate a first set of candidate parameters; convert the first set of candidate parameters into an adapted representation; define an adapted radiotherapy optimization problem as a function of the adapted representation such that a given solution to the adapted radiotherapy optimization problem estimates a solution to the radiotherapy optimization problem; process the adapted radiotherapy optimization problem to estimate a function of the solution to the adapted radiotherapy optimization problem; and process the estimated function of the solution to the adapted radiotherapy optimization problem to generate a deliverable radiotherapy treatment plan.

In some aspects, instantiating the first set of candidate parameters comprises a sampling process that generates candidate parameters according to at least one of a deterministic pattern and a probability distribution.

In some aspects, the sampling process is adapted based on at least one of user input or the radiotherapy optimization problem.

In some aspects, the instructions further configure the apparatus to process at least one of the radiotherapy optimization problem, previously generated candidate parameters and the function of the solution to the adapted radiotherapy optimization problem to generate a new set of candidate parameters.

In some aspects, the new set of candidate parameters are generated according to a parameter search optimization problem comprising a bilevel optimization problem.

In some aspects, the parameter search optimization problem is solved using a learned or non-learned optimization process including at least one of a machine learning model, a simplex method, an interior point method, a Newton method, a quasi-Newton method, a Gauss-Newton method, a Levenberg-Marquardt method, a linear least-squares method, a gradient descent method, a projected gradient method, a conjugate gradient method, an augmented Lagrangian method, a Nelder-Mead method, a branch and bound method, a cutting plane method, simulated anneal, or sequential quadratic programming.

In some aspects, the adapted representation is at least one of a tensor representation, a canonical form of the radiotherapy optimization problem, or a representation of the radiotherapy optimization problem by an algebraic modeling language.

In some aspects, the adapted radiotherapy optimization problem is processed by a machine learning model comprising a deep neural network, a convolutional neural network or a graph neural network.

In some aspects, the processing of the adapted radiotherapy optimization problem to estimate the function of the solution to the adapted radiotherapy optimization problem comprises at least one of a (i) a surrogate function, (ii) upper and lower bounds, (iii) an optimization solver halted before convergence, (iv) interpolation of already obtained results, or (v) a trained machine learning model.

In some aspects, the function of the solution to the adapted optimization problem comprises at least one of (i) the solution itself, (ii) a resulting dose distribution or dose-based metrics such as dose volume histogram (DVH) criteria, (iii) radiobiological effects, (iv) radiosurgical metrics such as coverage, selectivity or gradient index, (v) metrics quantifying a complexity of radiotherapy delivery, (vi) geometrical deviations, or (vii) sensitivity to uncertainties.

In some aspects, the instructions further configure the apparatus to at least one of: assess whether the estimated solution is tentatively acceptable; verify whether the estimated solution is deliverable; or process the estimated solution to generate a deliverable solution.

In some aspects, processing the estimated solution to generate a deliverable solution comprises solving the radiotherapy optimization problem exactly using the corresponding set of candidate parameters.

In some aspects, the instructions further configure the apparatus to: convert the function of the solution to the adapted radiotherapy optimization problem from a multi-dimensional tensor to a set of scalars.

In some aspects, the radiotherapy optimization problem comprises at least one of images of a patient or patient volume, a segmentation of the patient volume, a dose kernel, a dose volume histogram constraint, or a dose constraint.

In some aspects, the first set of candidate parameters are converted into an adapted representation based on an affine function.

In some aspects, converting the first set of candidate parameters into an adapted representation comprises mapping organ-specific parameters to voxel-specific parameters structured in a multi-dimensional grid corresponding to a patient geometry.

In some aspects, the first set of candidate parameters comprise weights and reference doses for each structure in a set of structures, the instructions further configure the apparatus to convert the first set of candidate parameters into a tensor representation by mapping the weights and reference doses to a tensor defined on a voxel grid and concatenating the tensor with dose maps defined on the same voxel grid.

In some aspects, processing the adapted radiotherapy optimization problem to estimate the function of the solution to the adapted radiotherapy optimization problem is performed in parallel or asynchronously.

In some aspects, the plurality of parameters are processed based on user input or automatically use an open-loop or closed-loop process.

In some aspects, the radiotherapy optimization problem is defined as:

$$x^*(w_S, \hat{d}_S) = \underset{x \in \Omega}{\mathrm{argming}}(x) + \sum_{S \in M} w_S \sum_{v \in S} f_S(\varphi_v^T x - \hat{d}_S)$$

where $x^* \in \Omega$ is a solution of the radiotherapy optimization problem, $\Omega$ is the feasible set, $w_S$ is a vector of weights for each structure S, $\varphi_v^T$ is a linear map of x to dose in a voxel v, $\hat{d}_S$ is a reference dose for structure S, and $g(x)$ and $f_S(x)$ are real-valued functions.

In some aspects, a non-transitory computer-readable storage medium, the computer-readable storage medium including instructions that when executed by a computer, cause the computer to: receive a radiotherapy optimization problem, the radiotherapy optimization problem comprising a plurality of parameters; process the radiotherapy optimization problem to instantiate a first set of candidate parameters; convert the first set of candidate parameters into an adapted representation; define an adapted radiotherapy optimization problem as a function of the adapted representation such that a given solution to the adapted radiotherapy optimization problem estimates a solution to the radiotherapy optimization problem; process the adapted radiotherapy optimization problem to estimate a function of the solution to the adapted radiotherapy optimization problem; and process the estimated function of the solution to the adapted radiotherapy optimization problem to generate a deliverable radiotherapy treatment plan.

The above overview is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
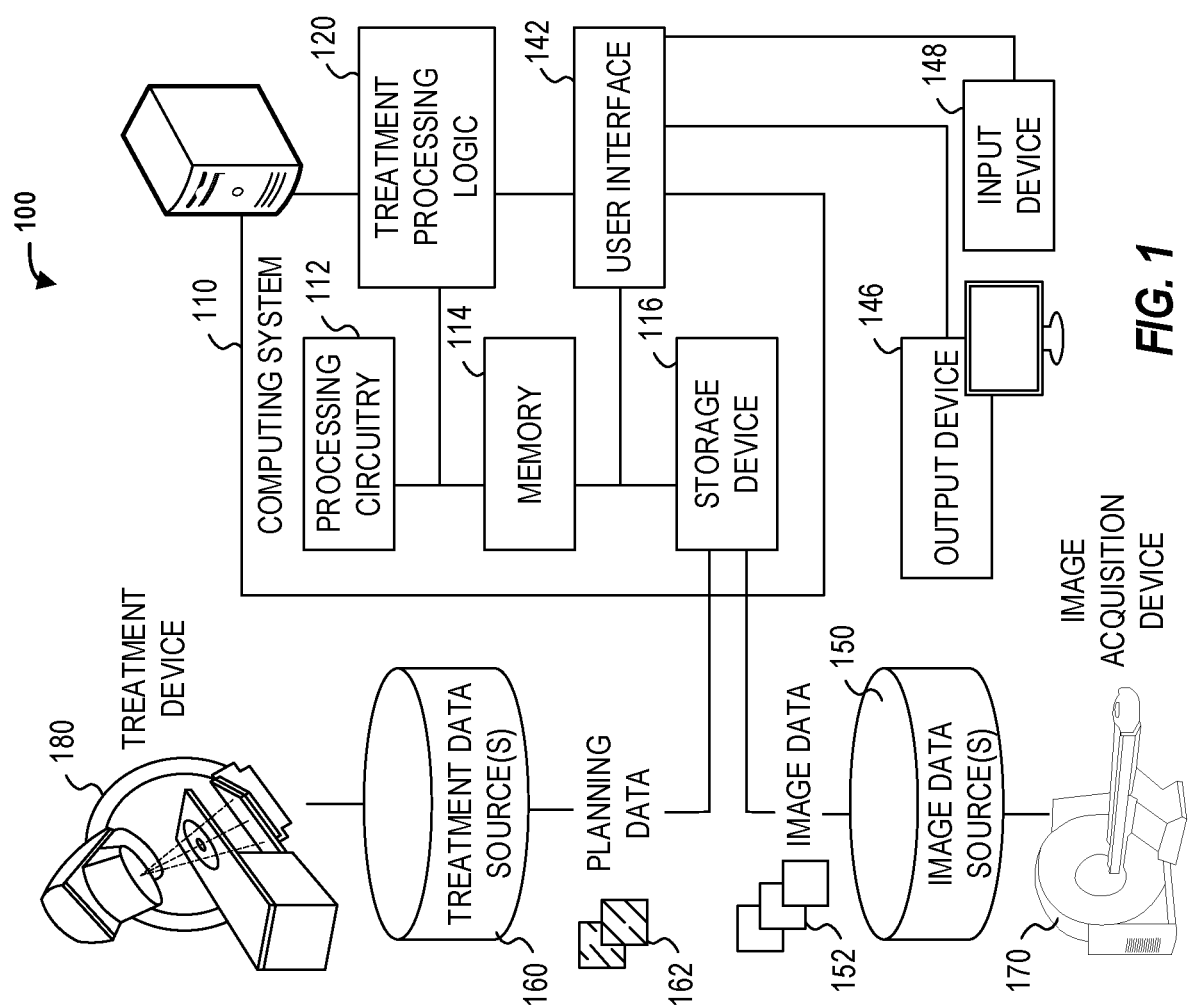
FIG. 1 illustrates an exemplary radiotherapy system adapted for performing treatment plan generation processing, according to some examples.

The present disclosure includes various techniques to generate radiotherapy treatment plans by instantiating a set of candidate parameters of a radiotherapy optimization problem and defining an adapted radiotherapy optimization problem based on an adapted representation of the set of candidate parameters. The adapted radiotherapy optimization problem is solved either exactly or approximately, such as using a machine learning model, to estimate a function of the solution to the adapted radiotherapy optimization problem. The technical benefits include reduced computing processing times to generate radiotherapy treatment plans, solving radiotherapy treatment plan optimization problems and accompanying improvements in processing, memory, and network resources used to generate radiotherapy treatment plans. These radiotherapy treatment plans may be applicable to a variety of medical treatment and diagnostic settings or radiotherapy treatment equipment and devices. Accordingly, in addition to these technical benefits, the present techniques may also result in many apparent medical treatment benefits (including improved accuracy of radiotherapy treatment, reduced exposure to unintended radiation, and the like).

Radiotherapy is one of the primary methods for treating cancer and is recommended for over 50% of all cancer patients. Treatment plans are created through a complex design process involving a mathematical optimization problem that captures the desirable characteristics of the dose delivery—typically requiring a sufficiently high dose to the target while minimizing the dose to healthy tissue. The overall structure of the optimization problem is the same for most forms of radiotherapy, including linac-based treatments (3D-CRT, IMRT, VMAT), proton treatments, Gamma Knife radiosurgery, and brachytherapy. The end result is the radiotherapy device configuration (e.g., control points) required to deliver the dose distribution.

Current planning software typically solve the minimization problem using standard mathematical optimization methods. These can be slow, causing unnecessary waiting for patients and clinicians. Future applications utilizing real-time imaging could even require real-time treatment planning, which cannot be performed using conventional optimization problem solvers. Specifically, in radiotherapy planning, treatment plans are usually generated by solving an optimization problem specified by a handful of global and organ-specific parameters. The essence of the problem is often to strike a balance between various conflicting objectives, such as high dose to target and low dose to sensitive organs. Such objectives are typically formulated as functions of the deviation between the planned dose and some reference dose and incorporated in the problem as a weighted sum. The weights and reference doses are examples of organ-specific parameters. There are also parameters that describe the treatment as a whole. Examples of such global parameters include aspects of the treatment geometry, such as the beam angles in a linear accelerator, the seed positions in brachytherapy or the isocenter locations in Gamma Knife radiosurgery, or the complexity of the treatment, e.g. the delivery time.

Finding acceptable parameter values is often a manual and tedious process of trial-and-error, especially so because evaluating a single choice of parameters requires solving the full optimization problem, which may take from a few seconds up to an hour depending on the application. In addition to being time-consuming, another problem of this process is the large variability in the final plan quality.

There are two principal ways of shortening the planning time: reducing the average time of an iteration and reducing the total number of iterations. To reduce the iteration time, a helpful observation is that in the parameter search phase—where the goal is merely to find an acceptable parameter setting—it may often be sufficient to approximate the solution of the optimization problem. An example of a way to approximate the solution is discussed in commonly-owned Adler et al. U.S. patent application Ser. No. 16/512,972, filed Jul. 16, 2019, which is incorporated by reference herein in its entirety. But the usefulness of this method depends on how much faster it is and whether the approximation is good enough, both of which, in turn, depend on whether the representation of the optimization problem matches a suitable neural network architecture. Also, the way to approximate the solution discussed in Adler makes no attempt at reducing the total number of iterations—it describes how to solve a given radiotherapy optimization problem, but not what problem to solve. This also relates to the problem with large variability, which mainly stems from the manual parameter search being heavily reliant on the planner's skills and preferences.

The typical representation of a treatment planning problem, where the parameters are represented as a set of a handful numbers, is not particularly well-suited for a neural network. In contrast, the dramatic successes that deep neural networks have had over the past few years have, to a large extent, been fuelled by tensor-based methods, and convolutional neural networks. Such methods exploit the local correlation structure of the input to learn powerful models using drastically fewer parameters, which means that they are less prone to overfitting and need less data to train effectively.

The disclosed techniques address these challenges and increase the speed and efficiency at which radiotherapy treatment plan optimization problems are solved. Specifically, the disclosed techniques solve radiotherapy optimization problems using three components: an explorer which determines a set of candidate parameters to evaluate; an adapter which converts the candidate parameters into adapted parameters that are represented in a fashion suitable for the solver; and a solver which computes an (approximate or exact) solution to the optimization problem defined by the adapted parameters. This approach reduces planning time and improves consistency by requiring fewer iterations in total and making each iteration faster. In some implementations, the explorer is iterative and the solver can be implemented as a machine learning model, in particular a convolutional neural network. In such cases, the adapter converts the parameters into a suitable adapted representation, such as a tensor-based representation.

In particular, the disclosed embodiments receive a radiotherapy optimization problem comprising a plurality of parameters and process the radiotherapy optimization problem to instantiate a first set of candidate parameters. The disclosed embodiments convert the first set of candidate parameters into an adapted representation and define an adapted radiotherapy optimization problem as a function of the adapted representation such that a given solution to the adapted optimization problem estimates a solution to the radiotherapy optimization problem. The disclosed embodiments process the adapted radiotherapy optimization problem to estimate a function of the solution to the adapted radiotherapy optimization problem and process the estimated function of the solution to the adapted optimization problem to generate a deliverable radiotherapy treatment plan.

FIG. 1 illustrates an exemplary radiotherapy system 100 adapted to perform radiotherapy plan processing operations using one or more of the approaches discussed herein. These radiotherapy plan processing operations are performed to enable the radiotherapy system 100 to provide radiation therapy to a patient based on specific aspects of captured medical imaging data and therapy dose calculations or radiotherapy machine configuration parameters. Specifically, the following processing operations may be implemented as part of the treatment processing logic 120. It will be understood, however, that many variations and use cases of the following trained models and treatment processing logic 120 may be provided, including in data verification, visualization, and other medical evaluative and diagnostic settings.

The radiotherapy system 100 includes a radiotherapy processing computing system 110 which hosts treatment processing logic 120. The radiotherapy processing computing system 110 may be connected to a network (not shown), and such network may be connected to the Internet. For instance, a network can connect the radiotherapy processing computing system 110 with one or more private and/or public medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device), and a treatment data source 160.

As an example, the radiotherapy processing computing system 110 can be configured to receive a treatment goal of a subject (e.g., from one or more MR images) and generate a radiotherapy treatment plan by executing instructions or data from the treatment processing logic 120, as part of operations to generate treatment plans to be used by the treatment device 180 and/or for output on device 146. In an embodiment, the treatment processing logic 120 solves an optimization problem to generate the radiotherapy treatment plan. In particular, the treatment processing logic 120 performs an iterative process by which different sets of candidate parameters are determined and converted to an adapted representation (e.g., a tensor based representation). The adapted representation is used to define an adapted radiotherapy optimization problem which can be solved in a number of ways to estimate a function of a solution to the radiotherapy optimization problem. In one example, a ML model is applied to the adapted optimization problem to estimate the function of the solution. In another example, the optimization problem is solved using a conventional optimization problem solver (e.g., simplex method, an interior point method, a Newton method, a quasi-Newton method, a Gauss-Newton method, a Levenberg-Marquardt method, a linear least-squares method, a gradient descent method, a projected gradient method, a conjugate gradient method, an augmented Lagrangian method, a Nelder-Mead method, a branch and bound method, a cutting plane method, simulated annealing, and/or sequential quadratic programming) based on the estimated optimization variables.

A generic radiotherapy treatment plan optimization problem can be defined as follows:

$$\operatorname*{minimize}_{x \in X} f(x)$$

$$\text{subject to } x \in \Omega$$

where $f: X \to \mathbb{R}$ is the objective function, $x \in X$ is the decision variables and $\Omega \subseteq X$ is the set of feasible variables. In general, the function $f$ can be nonlinear and the set $\Omega$ non-convex. The optimization problems are typically solved using some form of iterative scheme. For example, in case $f$ is smooth and convex, and $\Omega$ is convex, then the projected gradient scheme could be used to solve eq. (1) and reads as follows:

$$x_{n+1} = \operatorname{proj}_\Omega(x_n - \eta \nabla f(x_n))$$

where $\operatorname{proj}_\Omega: X \to X$ is the projection onto $\Omega$, $\eta \in \mathbb{R}$ is a stepsize and $\nabla f: X \to X$ the gradient. While these algorithms are typically provably convergent (e.g., given enough time (and correct parameter choices), the algorithm will converge to a minimizer), they are not always very fast and efficient. In fact, several algorithms may require hundreds if not thousands of iterations in order to achieve approximate convergence. Since each step may be computationally expensive, this may imply runtimes of minutes or even hours.

A typical example of a radiotherapy treatment planning problem is defined by Equation 1:

$$\operatorname*{minimize}_{x \geq 0} \sum_{S \in \mathcal{S}} w_S \sum_{v \in S} f_S(\varphi_v^T x - \hat{d}_S) \qquad (1)$$

where S is the collection of relevant structure sets, $f_S$ are convex functions, $\varphi_v$ is the part of the linear map (typically called dose rate kernel or dose influence matrix) that maps x to dose in voxel v, $\hat{d}_S$ is a reference dose for structure S, and the weight vector $w_S$ is nonnegative and sums to unity, i.e. $w_S \geq 0$ and $\Sigma_{S \in \mathcal{S}} w_S = 1$.

A solution to the optimization problem defined by Equation 1 is any vector x* that minimizes the objective function, among all choices that satisfy the constraints. The optimization problem can be seen as a (potentially multi-valued) function that maps parameters (for instance $(w_S, \hat{d}_S)$) to solutions defined by Equation 2:

$$x^*(w_S, \hat{d}_S) = \operatorname*{argmin}_{x \geq 0} g(x) + \sum_{S \in \mathcal{S}} w_S \sum_{v \in S} f_S(\varphi_v^T x - \hat{d}_S) \qquad (2)$$

According to the disclosed embodiments, an initial set of candidate parameters are solved for and determined by an explorer. In an embodiment, the explorer determines the next set of candidate parameters by minimizing a bilevel optimization problem defined by Equation 3:

$$\operatorname*{minimize}_{w_S, \hat{d}_S} R(x^*(w_S, \hat{d}_S))$$

$$\text{subject to } \sum_{S \in \mathcal{S}} w_S = 1,$$

$$w_S \geq 0,$$

$$\hat{d}_S \geq 0,$$

where R(x) is a cost function that encodes the decision-maker's preferences. In the preferred embodiment, the explorer is iterative; at iteration k, it generates candidate parameters $\eta^k$, e.g. $\eta^k = (w_S^k, \hat{d}_S^k)$.

The initial set of candidate parameters are provided to an adapter. The adapter converts these parameters into an adapted representation, such as a tensor representation. In an example, the adapter maps organ-specific parameters to voxel-specific parameters structured in a three-dimensional (3D) grid corresponding to the patient geometry. In the specific example of the optimization problem defined by Equation 1, this corresponds to exchanging $w_S$ for $w_{S,v}$ and moving $w_{S,v}$ inside the summation, as well as exchanging $\hat{d}_S$ for $\hat{d}_{S,v}$. This defines an adapted radiotherapy optimization problem.

In some implementations, the conversion to an adapted representation (e.g., tensor representation) can be performed exactly and efficiently when the optimization problem is separable with respect to a partition of the parameters and the partitions are naturally structured as a tensor. Tensors can be multi-dimensional blocks of numbers, which includes and generalizes the concepts of vectors and matrices to higher dimensions. For instance, in Equation 1, the objective function is separable across voxels which are in turn structured on a grid—the weights $w_{S,v}$ and reference doses $\hat{d}_{S,v}$ for each structure set S can each be represented on a 3D grid and concatenated along the fourth dimension, together with the dose maps $\varphi_v$.

The adapted radiotherapy optimization problem is provided to a solver to generate or predict a function of a solution to the radiotherapy optimization problem. In one example, the solver then takes this adapted representation, such as the tensor, as input, and uses a convolutional neural network to predict the solution or some property derived thereof. In some implementations, the solver is a (potentially stochastic or multi-valued) function that maps parameters to the solution. The solver may return the exact solution to the optimization problem or an approximated solution using the machine learning method discussed above with a deep convolutional neural network. In some implementations, the solver generates an approximated solution based on a surrogate function, upper and lower bounds, an optimization solver halted before convergence, or interpolation of already obtained results. In some cases, the solver may be capable of returning the gradient of the approximation with respect to the parameters. The system may contain multiple instances of solvers, which may be distributed, asynchronous and/or running in parallel. Each of the multiple instances of solvers may receive and generate a function of a solution based on a different set of candidate parameters that have been generated and adapted by the adapter.

The radiotherapy processing computing system 110 may include processing circuitry 112, memory 114, a storage device 116, and other hardware and software-operable features such as a user interface 142, a communication interface (not shown), and the like. The storage device 116 may store transitory or non-transitory computer-executable instructions, such as an operating system, radiation therapy treatment plans, training data, software programs (e.g., image processing software, image or anatomical visualization software, artificial intelligence (AI) or ML implementations and algorithms such as provided by deep learning models, ML models, and neural networks (NNs), etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application-specific integrated circuit (ASIC), a field programmable gate array (FPGA), a digital signal processor (DSP), a System on a Chip (SoC), or the like.

As would be appreciated by those skilled in the art, in some examples, the processing circuitry 112 may be a special-purpose processor rather than a general-purpose processor. The processing circuitry 112 may include one or more known processing devices, such as a microprocessor from the Pentium™, Core™ Xeon™, or Itanium® family manufactured by Intel™, the Turion™, Athlon™ Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry-based) or software-based processor (for example, a multi-core design or a plurality of processors each having a multi-core design). The processing circuitry 112 can execute sequences of transitory or non-transitory computer program instructions, stored in memory 114, and accessed from the storage device 116, to perform various operations, processes, and methods that will be explained in greater detail below. It should be understood that any component in system 100 may be implemented separately and operate as an independent device and may be coupled to any other component in system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, one or more ML model(s) or technique(s) parameters, data, or transitory or non-transitory computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting transitory or non-transitory machine-readable media.

The memory 114 and the storage device 116 may constitute a non-transitory computer-readable medium. For example, the memory 114 and the storage device 116 may store or load transitory or non-transitory instructions for one or more software applications on the computer-readable medium. Software applications stored or loaded with the memory 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory 114 and the storage device 116 may store or load an entire software application, part of a software application, or code or data that is associated with a software application, which is executable by the processing circuitry 112. In a further example, the memory 114 and the storage device 116 may store, load, and manipulate one or more radiation therapy treatment plans, imaging data, segmentation data, treatment visualizations, histograms or measurements, one or more AI model data (e.g., weights and parameters of the ML model(s) of the disclosed embodiments), training data, labels and mapping data, and the like. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, the network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., MR images) for hosting on the storage device 116 and the memory 114. In yet another example, the software programs may substitute functions of the patient images such as signed distance functions or processed versions of the images that emphasize some aspect of the image information.

In an example, the radiotherapy processing computing system 110 may obtain or communicate image data 152 from or to image data source 150. In further examples, the treatment data source 160 receives or updates the planning data 162 as a result of a treatment plan generated by the treatment processing logic 120. The image data source 150 may also provide or host the imaging data for use in the treatment processing logic 120.

In an example, computing system 110 may communicate with treatment data source(s) 160 and input device 148 to generate pairs of one or more training optimization variables and training parameters of a plurality of training radiotherapy treatment plan optimization problems; pairs of one or more training optimization variables and training parameters of a plurality of training radiotherapy treatment plan optimization problems and solutions to the plurality of training radiotherapy treatment optimization problems; and pairs of one or more training optimization variables and training parameters of a plurality of training radiotherapy treatment plan optimization problems of a given type.

The processing circuitry 112 may be communicatively coupled to the memory 114 and the storage device 116, and the processing circuitry 112 may be configured to execute computer-executable instructions stored thereon from either the memory 114 or the storage device 116. The processing circuitry 112 may execute instructions to cause medical images from the image data 152 to be received or obtained in memory 114 and processed using the treatment processing logic 120 to generate a treatment plan.

In addition, the processing circuitry 112 may utilize software programs to generate intermediate data such as updated parameters to be used, for example, by a NN model, machine learning model, treatment processing logic 120 or other aspects involved with generation of a treatment plan as discussed herein. Further, such software programs may utilize the treatment processing logic 120 to produce new or updated treatment plan parameters for deployment to the treatment data source 160 and/or presentation on output device 146, using the techniques further discussed herein. The processing circuitry 112 may subsequently then transmit the new or updated treatment plan parameters via a communication interface and the network to the treatment device 180, where the radiation therapy plan will be used to treat a patient with radiation via the treatment device 180, consistent with results of the trained ML model implemented by the treatment processing logic 120.

In the examples herein, the processing circuitry 112 may execute software programs that invoke the treatment processing logic 120 to implement functions of ML, deep learning, NNs, and other aspects of artificial intelligence for treatment plan generation from an input radiotherapy medical information (e.g., CT image, MR image, and/or sCT image and/or dose information). For instance, the processing circuitry 112 may execute software programs that train, analyze, predict, evaluate, and generate a treatment plan parameter from received radiotherapy medical information as discussed herein.

In an example, the image data 152 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer-generated synthetic images (e.g., pseudo-CT images) and the like. Further, the image data 152 may also include or be associated with medical image processing data (for example, training images, ground truth images, contoured images, and dose images). In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., a MRI device combined with a linear accelerator, also referred to as an "MRI-Linac"). Such an MRI-Linac can be used, for example, to determine a location of a target organ or a target tumor in the patient so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, including control points of a radiotherapy treatment device, such as couch position, beam intensity, beam angles, dose-histogram-volume information, the number of radiation beams to be used during therapy, the dose per beam, and the like.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information (e.g., control points) may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.), treatment plans, a target, localizing a target and/or tracking a target, or any related information to the user. The input device 148 connected to the user interface 142 may be a keyboard, a keypad, a touch screen or any type of device that a user may use to access the radiotherapy system 100. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system 100 may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D CBCT or CT or MRI volume. Such 2D slices can be acquired by the image acquisition device 170 in "near real time" while a patient is undergoing radiation therapy treatment (for example, when using the treatment device 180 (with "near real time" meaning acquiring the data in at least milliseconds or less)).

The treatment processing logic 120 in the radiotherapy processing computing system 110 implements a ML model, which involves the use of a trained (learned) ML model. This ML model may be provided by a NN trained as part of a NN model. One or more teacher ML models may be provided by a different entity or at an off-site facility relative to treatment processing logic 120 and is accessible by issuing one or more queries to the off-site facility.

Supervised machine learning (ML) algorithms or ML models or techniques can be summarized as function approximation. Training data consisting of input-output pairs of some type (e.g., one or more training optimization variables and training parameters of a plurality of training radiotherapy treatment plan optimization problems) are acquired from, e.g., expert clinicians or prior optimization plan solvers and a function is "trained" to approximate this mapping. Some methods involve NNs. In these, a set of parametrized functions $A_\theta$ are selected, where $\theta$ is a set of parameters (e.g., convolution kernels and biases) that are selected by minimizing the average error over the training data. If the input-output pairs are denoted by $(x_m, y_m)$, the function can be formalized by solving a minimization problem:

$$\min_\theta \sum_{m=1}^{M} \|A_\theta(x_m) - y_m\|^2$$

Once the network has been trained (e.g., $\theta$ has been selected), the function $A_\theta$ can be applied to any new input. For example, in the above setting of radiotherapy treatment plan optimization problem variables, a never-before-seen adapted radiotherapy treatment plan optimization problem can be fed into $A_\theta$, and one or more functions of solutions to the original radiotherapy treatment plan optimization problem are estimated that match what an optimization problem solver would find.

Simple NNs consist of an input layer, a middle or hidden layer, and an output layer, each containing computational units or nodes. The hidden layer(s) nodes have input from all the input layer nodes and are connected to all nodes in the output layer. Such a network is termed "fully connected." Each node communicates a signal to the output node depending on a nonlinear function of the sum of its inputs. For a classifier, the number of input layer nodes typically equals the number of features for each of a set of objects being sorted into classes, and the number of output layer nodes is equal to the number of classes. A network is trained by presenting it with the features of objects of known classes and adjusting the node weights to reduce the training error by an algorithm called backpropagation. Thus, the trained network can classify novel objects whose class is unknown.

Neural networks have the capacity to discover relationships between the data and classes or regression values, and under certain conditions, can emulate any function $y=f(x)$ including non-linear functions. In ML, an assumption is that the training and test data are both generated by the same data-generating process, $p_{data}$, in which each $\{x_i, y_i\}$ sample is identically and independently distributed (i.i.d.). In ML, the goals are to minimize the training error and to make the difference between the training and test errors as small as possible. Underfitting occurs if the training error is too large; overfitting occurs when the train-test error gap is too large. Both types of performance deficiency are related to model capacity: large capacity may fit the training data very well but lead to overfitting, while small capacity may lead to underfitting.

Figure 2A:
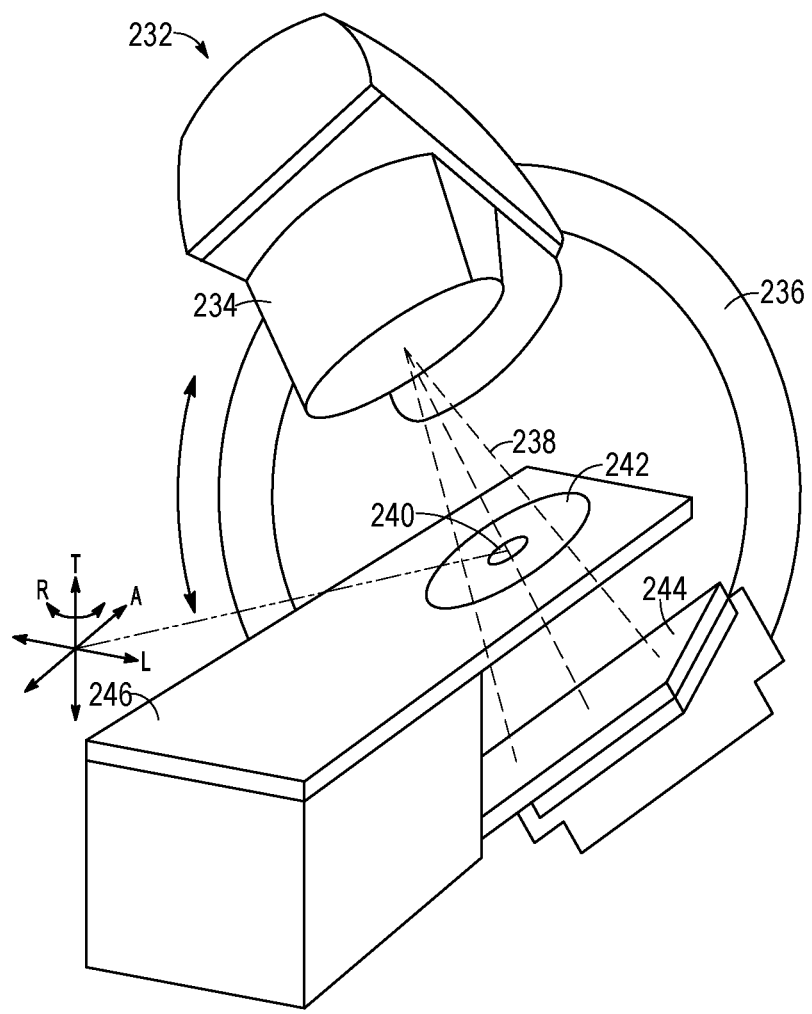
FIG. 2A illustrates an exemplary image-guided radiotherapy device, according to some examples of the disclosure.

FIG. 2A illustrates an exemplary image-guided radiation therapy device 232 that includes a radiation source, such as an X-ray source or a linear accelerator, a couch 246, an imaging detector 244, and a radiation therapy output 234. The radiation therapy device 232 may be configured to emit a radiation therapy beam 238 to provide therapy to a patient. The radiation therapy output 234 can include one or more attenuators or collimators, such as a MLC.

As an example, a patient can be positioned in a region 242, supported by the treatment couch 246, to receive a radiation therapy dose according to a radiation therapy treatment plan. The radiation therapy output 234 can be mounted or attached to a gantry 236 or other mechanical support. One or more chassis motors (not shown) may rotate the gantry 236 and the radiation therapy output 234 around the couch 246 when the couch 246 is inserted into the treatment area. In an example, gantry 236 may be continuously rotatable around couch 246 when the couch 246 is inserted into the treatment area. In another example, gantry 236 may rotate to a predetermined position when the couch 246 is inserted into the treatment area. For example, the gantry 236 can be configured to rotate the therapy output 234 around an axis ("A"). Both the couch 246 and the radiation therapy output 234 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 246's movements or rotations in order to properly position the patient in or out of the radiation therapy beam 238, according to a radiation therapy treatment plan. Both the couch 246 and the gantry 236 are independently moveable from one another in multiple degrees of freedom, which allows the patient to be positioned such that the radiation therapy beam 238 can precisely target the tumor.

The coordinate system (including axes A, T, and L) can have an origin located at an isocenter 240. The isocenter 240 can be defined as a location where the central axis of the radiation therapy beam 238 intersects the origin of a coordinate axis, such as to deliver a prescribed radiation dose to a location on or within a patient. Alternatively, the isocenter 240 can be defined as a location where the central axis of the radiation therapy beam 238 intersects the patient for various rotational positions of the radiation therapy output 234 as positioned by the gantry 236 around the axis A.

Gantry 236 may also have an attached imaging detector 244. The imaging detector 244 is preferably located opposite to the radiation source (output 234) and, in an example, the imaging detector 244 can be located within a field of the therapy beam 238. The imaging detector 244 can be mounted on the gantry 236, preferably opposite the radiation therapy output 234, so as to maintain alignment with the radiation therapy beam 238. The imaging detector 244 rotates about the rotational axis as the gantry 236 rotates. In an example, the imaging detector 244 can be a flat panel detector (e.g., a direct detector or a scintillator detector). In this manner, the imaging detector 244 can be used to monitor the radiation therapy beam 238, or the imaging detector 244 can be used for imaging the patient's anatomy, such as portal imaging. The control circuitry of radiation therapy device 232 may be integrated within the radiotherapy system 100 or remote from it.

In an illustrative example, one or more of the couch 246, the therapy output 234, or the gantry 236 can be automatically positioned, and the therapy output 234 can establish the therapy beam 238 according to a specified dose for a particular therapy delivery instance. A sequence of therapy deliveries can be specified according to a radiation therapy treatment plan, such as using one or more different orientations or locations of the gantry 236, couch 246, or therapy output 234. The therapy deliveries can occur sequentially but can intersect in a desired therapy locus on or within the patient, such as at the isocenter 240. A prescribed cumulative dose of radiation therapy can thereby be delivered to the therapy locus while damage to tissue nearby the therapy locus can be reduced or avoided.

Thus, FIG. 2A specifically illustrates an example of a radiation therapy device 232 operable to provide radiotherapy treatment to a patient consistent with or according to a radiotherapy treatment plan, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, and the like, as would be recognized by one of ordinary skill in the art.

Figure 2B:
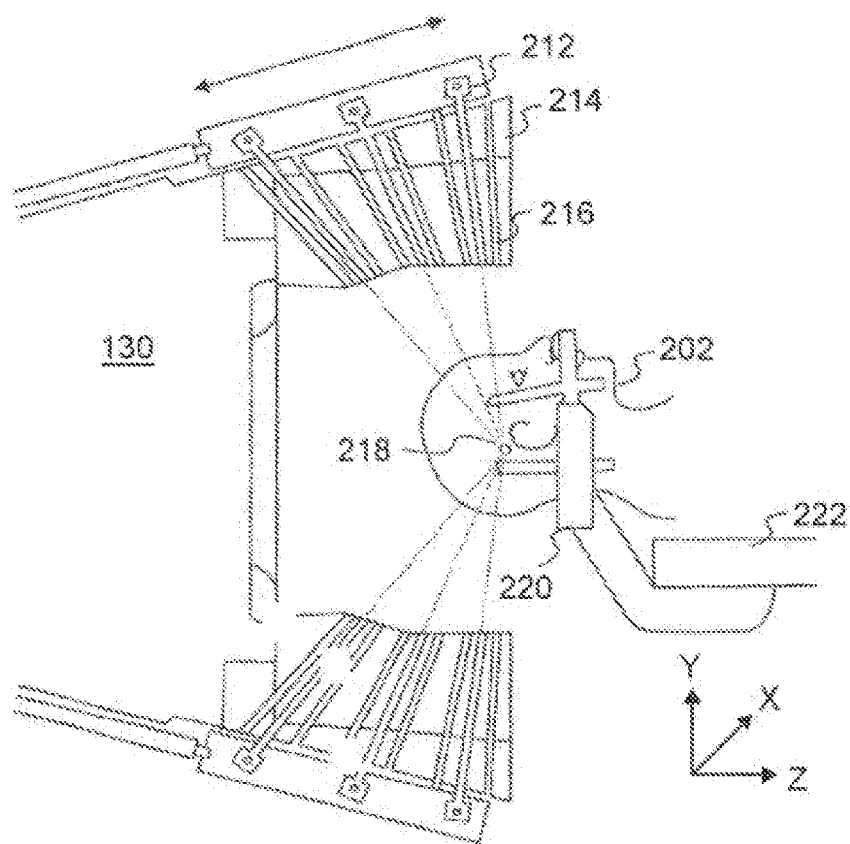
FIG. 2B illustrates a radiation therapy device, a Gamma Knife, according to some examples of the disclosure.

FIG. 2B illustrates a radiotherapy device 130, a Gamma Knife in which the present disclosure can be used. A patient 202 may wear a coordinate frame 220 to keep stable the patient's body part (e.g. the head) undergoing surgery or radiotherapy. Coordinate frame 220 and a patient positioning system 222 may establish a spatial coordinate system, which may be used while imaging a patient or during radiation surgery. Radiotherapy device 130 may include a protective housing 214 to enclose a plurality of radiation sources 212 for generation of radiation beams (e.g. beamlets) through beam channels 216. The plurality of beams may be configured to focus on an isocenter 218 from different locations. While each individual radiation beam may have relatively low intensity, isocenter 218 may receive a relatively high level of radiation when multiple doses from different radiation beams accumulate at isocenter 218. In certain embodiments, isocenter 218 may correspond to a target under surgery or treatment, such as a tumor.

As an example of an embodiment, an output element may include a dose to be applied to a voxel of a particular OAR. Further, a feature element may be used to determine the output element. The feature element may include a distance between the voxel in the OAR and the closest boundary voxel in a target tumor. Therefore, the feature element may include a signed distance x indicating the distance between a voxel in an OAR and the closest boundary voxel in a target for the radiation therapy. The output element may include a dose D in the voxel of the OAR from which x is measured. In some other embodiments, each training sample may correspond to a particular voxel in the target or OAR, such that multiple training samples within the training data correspond to the whole volume of the target or OAR and other anatomical portions subject to the radiotherapy treatment.

In some implementations, the new radiotherapy treatment plan optimization problem (that includes at least one of images of a patient or patient volume, a segmentation of the patient volume, a dose kernel, a dose volume histogram constraint, or a dose constraint) can be solved using the estimated optimization variables that are provided by the ML model. The solution to the optimization problem includes at least one of radiotherapy device parameters, fluence maps, shot positions, or beam-on times. In certain cases, to further simplify solving the new radiotherapy treatment plan optimization problem that is constrained (e.g., an optimization problem that is subject to certain constraints), the new radiotherapy treatment plan optimization problem can be first converted to an unconstrained optimization problem. This may be done before, during, or after the optimization variables are estimated by the ML model for the new radiotherapy treatment plan optimization problem. To represent the constrained radiotherapy treatment plan optimization problem as an unconstrained optimization problem, a merit function can be used. If the optimization problem is converted to an unconstrained optimization problem before estimating the optimization variables by the ML model, the unconstrained optimization problem can be processed by the ML model to estimate the optimization variables of the new optimization problem that are then used to solve the new optimization problem.

Figure 3:
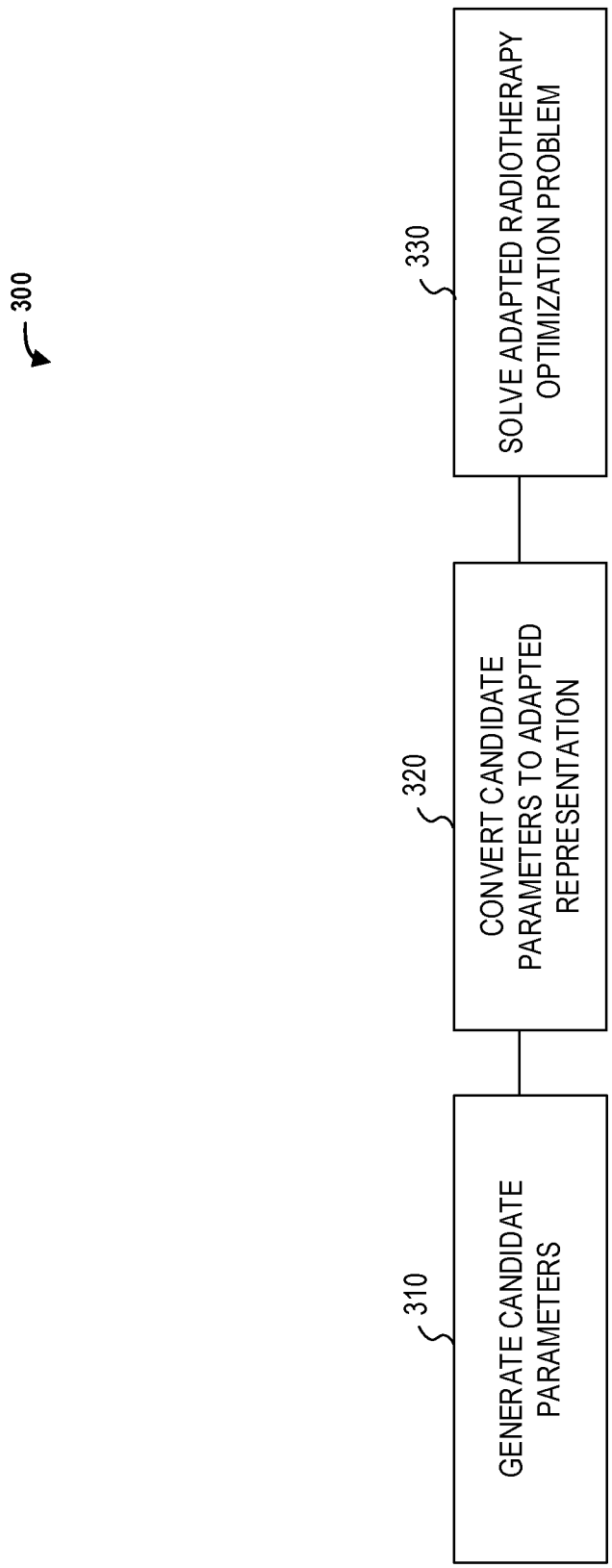
FIG. 3 illustrates an exemplary data flow for solving a radiotherapy treatment plan optimization problem (radiotherapy optimization problem), according to some examples of the disclosure.

FIG. 3 illustrates an exemplary data flow 300 for solving a radiotherapy treatment plan optimization problem (radiotherapy optimization problem), according to some examples of the disclosure. In some embodiments, a radiotherapy optimization problem is received. For example, a set of candidate parameters can initially be determined by solving a first optimization problem. These candidate parameters are converted to a suitable form for solving a second optimization problem (e.g., a radiotherapy optimization problem). The second optimization problem is solved to estimate a function of a solution to the radiotherapy optimization problem. The estimated function of the solution is converted back to a form suitable for processing by the first optimization problem. Another iteration is then performed for solving the first optimization problem based on the estimated function of the solution.

An explorer 310 performs an operation to generate an initial set of candidate parameters. In some implementations, the explorer 310 is a decision-making person, algorithm or hybrid thereof which determines what candidate parameters of the optimization problem to evaluate. The candidate parameters may include one or multiple parameter settings to evaluate.

The explorer 310 may be iterative, in which case it may halt when a stopping criteria is met or it is interrupted. The decision-making may be informed by intermediate results, such as a closed-loop feedback system, or determined in advance, such as in an open-loop fashion. The explorer 310 may be deterministic, e.g. evaluating parameters in a predetermined pattern such as a grid (an open-loop method) or by maximizing an expected improvement such as in Bayesian optimization (a closed-loop method), or it may be stochastic, e.g. an open-loop method such as randomly sampling a predetermined probability distribution or a closed-loop method such as simulated annealing.

Certain algorithmic elements of the explorer 310 may be fully automatic, where the decision-making is not directed by any human input. This case includes the so called no-preference methods. In some cases, human input may be received before, during or after the explorer 310 runs to generate the initial set of candidate parameters, and examples of corresponding classes of methods are referred to as a priori, interactive or a posteriori, respectively.

A priori methods may need sufficient preference information to be expressed before the explorer 310 runs. Some examples of a priori methods include the utility function method, lexicographic method, wishlists, and goal programming. In interactive methods, the solution process is iterative and the human decision maker continuously interacts with the method when searching for the most preferred solution. In other words, the human decision maker is expected to express preferences at each iteration in order to guide the parameter search and learn what kind of solutions are attainable. As an example, each solution or set of parameters generated by the explorer 310 are output and presented to the user (human decision maker) to approve, deny, or adjust the parameters before providing them to the adapter 320.

A posteriori methods aim at producing all, or at least a representative subset of, the Pareto optimal solutions. Most a posteriori methods are based on either mathematical programming or evolutionary algorithms. Some examples of mathematical programming-based methods include the Normal Boundary Intersection (NBI), Normal Constraint (NC), Successive Pareto Optimization (SPO) and Directed Search Domain (DSD). Well-known evolutionary algorithms include Non-dominated Sorting Genetic Algorithm-II (NSGA-II), Strength Pareto Evolutionary Algorithm 2 (SPEA-2), particle swarm optimization and simulated annealing.

In some embodiments, algorithmic elements of the explorer 310 may be parameterized by trainable parameters, which may be trained using supervised, unsupervised or reinforcement learning. Namely, the explorer 310 can be implemented by a machine learning model that is trained based on a loss function. The loss function may be determined from preferences determined a priori, or it may quantify the usability of the human interaction, e.g. the wall clock time required to reach a satisfactory solution. The parameters may be trained based on gradients of a loss with respect to the parameters. In particular, if all components in the system are differentiable, the machine learning model of the explorer 310 may be trained in an end-to-end fashion. If both the explorer 310 and the solver 330 contain trainable parameters, the explorer 310 and/or the solver 330 may be trained using meta-learning.

In some implementations, the explorer 310 provides the initial set of candidate parameters to an adapter 320. The adapter 320 converts the candidate parameters to an adapted representation, such as a tensor-based representation, a canonical form of the optimization problem, or a representation of the optimization problem by an algebraic modelling language. The adapted representation is used to define the radiotherapy optimization problem as an adapted radiotherapy optimization problem. The adapter 320 provides the adapted radiotherapy optimization problem to the solver 330 to generate or predict one or more functions of a solution to the original radiotherapy optimization problem. The function of the solution to the adapted optimization problem can include at least one of (i) the solution itself, (ii) a resulting dose distribution or dose-based metrics such as dose volume histogram (DVH) criteria, (iii) radiobiological effects, (iv) radiosurgical metrics such as coverage, selectivity or gradient index, (v) metrics quantifying a complexity of radiotherapy delivery, (vi) geometrical deviations, or (vii) sensitivity to uncertainties.

In an embodiment, the adapter 320 converts the parameters from an input domain into a representation in an output domain suitable for the solver 330, for instance a tensor-based representation or a canonical form of the optimization problem. The adaptation may also include various pre-processing steps, such as normalization and cropping. The input domain and output domain may be the same, for instance as a result of pre-processing, or different, for instance if a set of scalars are converted into a 3D tensor. The adapter 320 may be differentiable, in which it may be possible to compute the gradient of the adapter 320 output with respect to its input. For example, the adapter 320 may be an affine function. The adapter 320 may be lossy, in which case the adapter 320 discards some of the information in the input. The adapter 320 may also be able to map adapted parameters or solutions back to the input domain to provide the adapted solution to the explorer 310 for evaluation.

In some implementations, the adapter 320 can perform a dimensionality reduction process to convert the initial set of candidate parameters to the adapted representation. For example, the adapter 320 can perform one or more of principal component analysis (PCA), t-SNE, autoencoder, or some classical computer vision method. For example, the adapter 320 can perform operations including resizing, de-texturize, de-colorize, edge enhancement, salient edge map, local phase, flip, rotate, cropping, image registration, and/or a machine learning method, e.g. a convolutional neural network to generate the adaptation of the initial set of candidate parameters. Further, the adapter 320 may perform a classical pre-processing method for the medical imaging modality associated with the optimization problem or initial set of candidate parameters including: bias-field correction, intensity normalization, distortion correction, and/or denoising.

The interaction with the adapter 320 and solver 330 may be synchronous. In this case, the adapter 320 waits until the solver 330 and the explorer 310 complete an iteration to determine a solution to the radiotherapy optimization problem before making a new decision. In some implementations, the adapter 320 may be asynchronous, in which case a message-based system is used to queue job requests while operating continuously. The solver 330 may run concurrently with the explorer 310 or after the explorer 310 has halted.

In some implementations, multiple instances of explorers 310 running in parallel and communicating with each other, e.g. as a federated learning system, can be provided. In such cases, each explorer 310 can determine a different set of candidate parameters based on prior solutions to the optimization problem provided by the solver 330. Each of the different sets of candidate parameters are provided sequentially or in parallel to the adapter 320 to generate one or more adapted radiotherapy optimization problems. The adapter 320 can queue each of the adapted radiotherapy optimization problems for the solver 330 to solve. In some cases, the adapter 320 can provide multiple adapted radiotherapy optimization problems in parallel to multiple solvers 330 to solve in parallel.

The adapter 320 can receive the function of the solution from each of the solvers 330. The adapter 320 converts the function of the solution from one representation to another, suitable for the explorer 310 to operate on. For example, the adapter 320 can convert the function of the solution to the adapted radiotherapy optimization problem from a multi-dimensional tensor to a set of scalars. The set of scalars are then processed by the explorer 310 to generate and instantiate a second set of candidate parameters. The second set of candidate parameters are then again adapted by the adapter 320 and used to generate an adapted radiotherapy optimization problem for the solver 330 to solve.

In some cases, prior to generating the second set of candidate parameters, the explorer 310 assesses whether the estimated solution is tentatively acceptable or verifies whether the estimated solution is deliverable in response to determining that the estimated solution is tentatively acceptable. In some embodiments, the explorer 310 verifies whether the estimated solution is deliverable in response to assessing that the estimated solution is tentatively acceptable (e.g., the estimated solution satisfies one or more criteria).

In some implementations, the process by which the explorer 310 processes the estimated solution to generate a deliverable solution includes solving the radiotherapy optimization problem exactly using the corresponding set of candidate parameters. For example, the explorer 310 can obtain a first initial set of candidate parameters used by the adapter 320 to generate the adapted radiotherapy optimization problem. The explorer 310 then receives the function of the solution generated by the solver 330 processing the adapted radiotherapy optimization problem. The explorer 310 can then solve the radiotherapy optimization problem exactly based on the function obtained from the solver 330 and/or the first set of candidate parameters. The exact solution can provide the deliverable solution.

Figure 4:
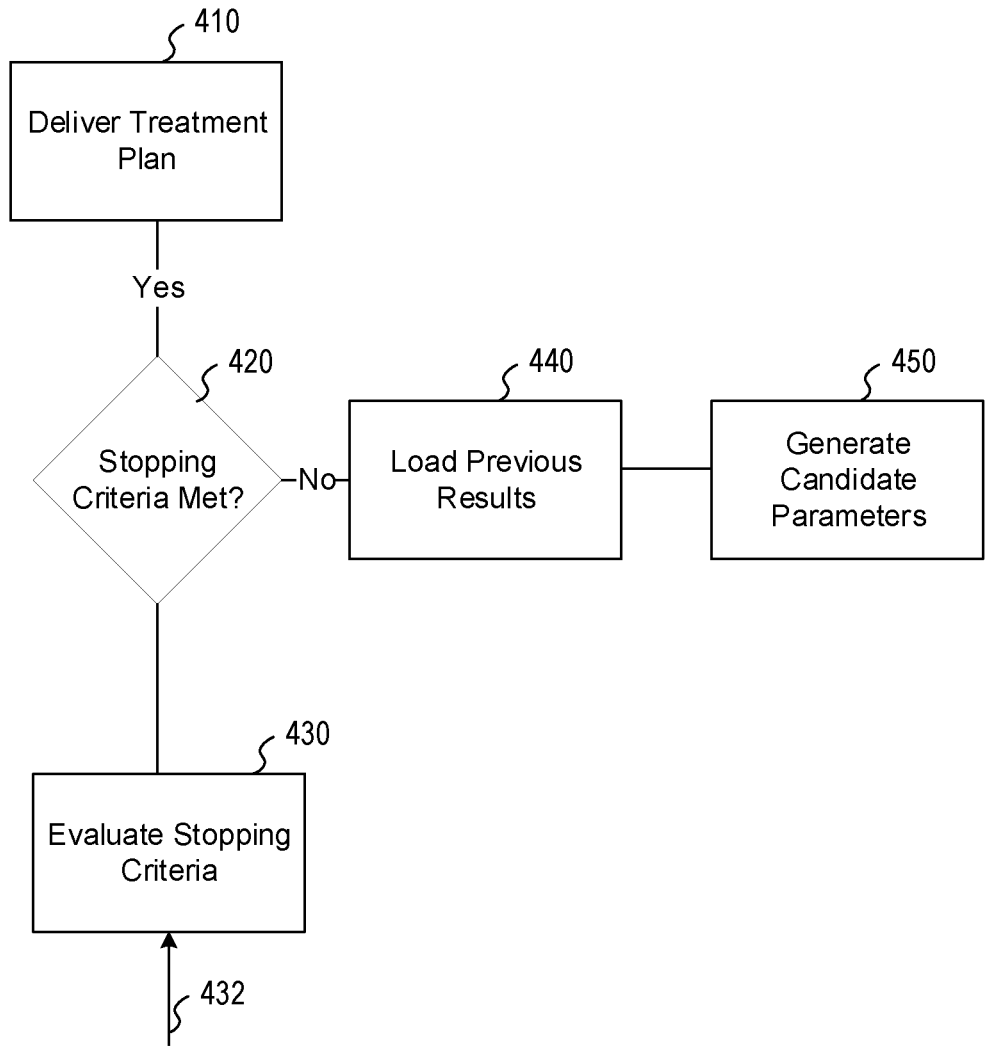
FIG. 4 illustrates an exemplary data flow for generating candidate parameters of the radiotherapy optimization problem, according to some examples of the disclosure.

FIG. 4 illustrates an exemplary data flow of the explorer 310 for generating candidate parameters of the radiotherapy optimization problem, according to some examples of the disclosure. The explorer 310 initially receives a radiotherapy optimization problem. The explorer 310 loads previous results 440 for the radiotherapy optimization problem. For example, the explorer 310 loads one or more solutions or functions of solutions to the radiotherapy optimization problem and/or previously generated candidate parameters of the radiotherapy optimization problem. The explorer 310 performs operations, discussed above, to generate a first set of candidate parameters 450. This first set candidate parameters 450 are provided to the adapter 320.

For example, the explorer 310 generates an initial set of candidate parameters by, for example, performing a sampling process that generates candidate parameters according to at least one of a deterministic pattern and a probability distribution, such as minimizing a bilevel optimization problem defined by Equation 3. In some cases, the sampling process is adapted based on at least one of user input or the radiotherapy optimization problem. The adapter 320 generates adapted candidate parameters based on the first set of candidate parameters and defines an adapted radiotherapy optimization problem based on the adapted candidate parameters. For example, the adapter 320 converts these parameters into an adapted representation, such as a tensor representation. In an example, the adapter maps organ-specific parameters to voxel-specific parameters structured in a three-dimensional (3D) grid corresponding to the patient geometry. In the specific example of the optimization problem defined by Equation 1, this corresponds to exchanging $w_S$ for $w_{S,v}$ (voxel-wise weight) and moving $w_{S,v}$ inside the summation, as well as exchanging $\hat{d}_S$ for $\hat{d}_{S,v}$ (voxel-wise dose). This defines an adapted radiotherapy optimization problem, such as the problem defined by Equation 2 in which the $w_S$ is exchanged for $w_{S,v}$ and moved inside the summation and $\hat{d}_S$ is exchanged for $\hat{d}_{S,v}$. Namely, the explorer 310 generates a set of voxel-wise weights and voxel-wise dose parameters that are then used to solve the radiotherapy optimization problem. These voxel-wise weights and dose parameters in scaler form are converted to a tensor representation to be substituted in the radiotherapy optimization problem.

The adapter 320 schedules a job for the solver 330 to solve. The solver 330 provides the function of the solution to the adapted radiotherapy optimization problem back to the adapter 320. The adapter 320 converts the function of the solution to a domain or a suitable representation for processing by the explorer 310. Namely, the adapter 320 generates an adapted representation of the solution 432 which is provided to the explorer 310.

The explorer 310 receives the adapted representation of the solution 432 and evaluates the adapted representation of the solution 432 against a stopping criteria 430. For example, the stopping criteria can include a maximum number of iterations, a decrease in objective value is achieved, a step length is met, a solution being within a specified threshold error of a final solution to the given optimization problem, or is within a specified threshold error of the solution after the specified number of iterations. In some cases, the explorer 310 assesses or verifies whether the adapted representation of the solution 432 is tentatively acceptable or deliverable. If so, the explorer 310 determines that the stopping criteria is met in decision block 420 and delivers the treatment plan 410.

Figure 5:
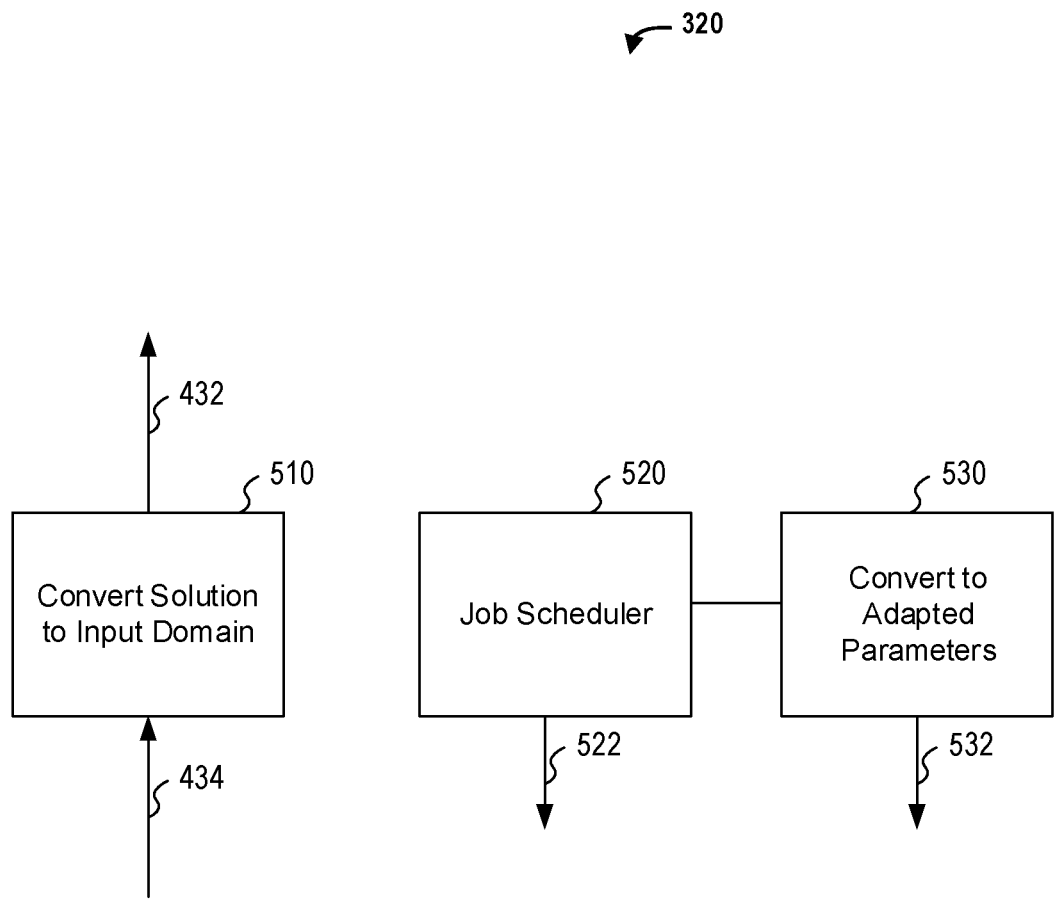
FIG. 5 illustrates an exemplary data flow for converting candidate parameters of the radiotherapy optimization problem to adapted parameters, according to some examples of the disclosure.

FIG. 5 illustrates an exemplary data flow of the adapter 320 for converting candidate parameters of the radiotherapy optimization problem to adapted parameters, according to some examples of the disclosure. Specifically, the adapter 320 includes a processing block 530 that converts the candidate parameters received from the explorer 310 to an adapted representation, such as a tensor-based representation. The adapted representation is used by the processing block 530 to define an adapted radiotherapy optimization problem 532.

The adapter 320 includes a job scheduler processing block 520 that instructs one or more solvers 330 to solve the adapted radiotherapy optimization problem 532. For example, if there are multiple instances of solvers 330, the job scheduler processing block 520 indicates which solver 330 is set to solve which adapted radiotherapy optimization problem 532. As an example of an asynchronous embodiment, the scheduler could maintain a queue of adapted radiotherapy optimization problems to solve, which a solver fetches a new job from when it has completed a job (if the queue is empty it may try again after a certain time has elapsed).

The adapter 320 receives a function of a solution to the radiotherapy optimization problem from the one or more solvers 330. The adapter 320 includes a processing block 510 that converts the function of the solution to a domain or solution 432 suitable for the explorer 310.

Figure 6:
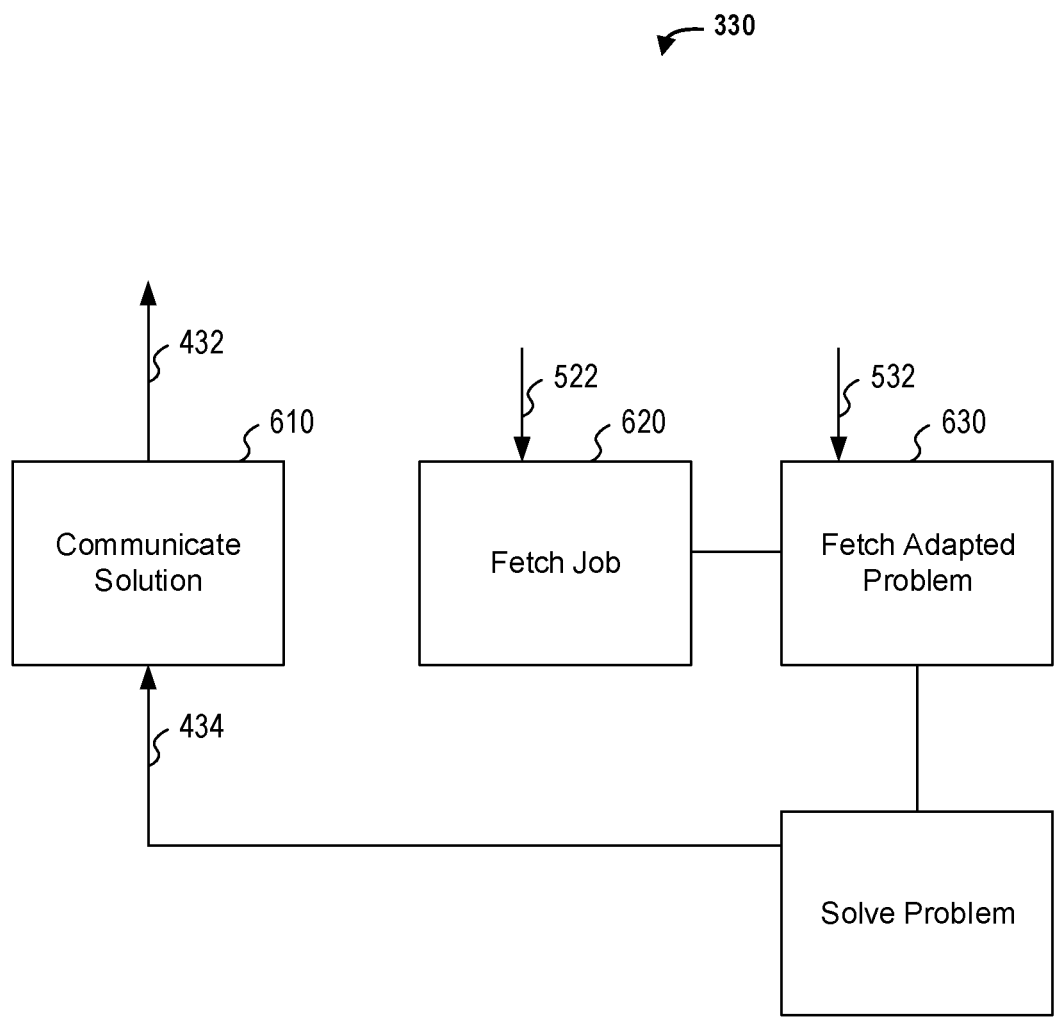
FIG. 6 illustrates an exemplary data flow for solving an adapted radiotherapy optimization problem, according to some examples of the disclosure.

FIG. 6 illustrates an exemplary data flow of the solver 330 for solving an adapted radiotherapy optimization problem, according to some examples of the disclosure. The solver 330 includes a fetch job processing block 620 that receives instructions 522 from the adapter 320. The instructions 522 indicate to the solver 330 which adapted radiotherapy optimization problem 532 to solve. In this way, different instances of the solvers 330 can in parallel operate to solve adapted radiotherapy optimization problems with different sets of candidate parameters provided by the explorer 310.

Each solver 330 includes a fetch adapted problem processing block 630 which obtains from the adapter 320 the adapted radiotherapy optimization problem 532. The adapted radiotherapy optimization problem 532 is provided to a solve problem block which generates a function of a solution to the adapted radiotherapy optimization problem 532, such as by approximating a solution 434 using a machine learning model. This approximated solution 434 is provided to a communicate solution processing block 610 to be provided to the adapter 320 and/or directly to the explorer 310.

After the explorer 310 evaluates the approximated solution 434 against the stopping criteria, the explorer 310 can generate a second set of candidate parameters. The second set of candidate parameters can similarly be provided to the adapter 320 and then to the solver 330 to generate another approximated solution 434. This process continues until a stopping criteria is reached by the explorer 310. In some cases multiple explorers 310 operate in parallel or sequentially with the solvers 330 to generate different sets of candidate parameters.

These different sets of candidate parameters are processed by the adapter 320 to generate different sets of adapted radiotherapy optimization problems 532. In case a single solver 330 is implemented, these different sets of adapted radiotherapy optimization problems are processed sequentially by the solver 330. In case of multiple solvers 330, the multiple solvers operate in parallel to process the multiple adapted radiotherapy optimization problems.

Figure 7:
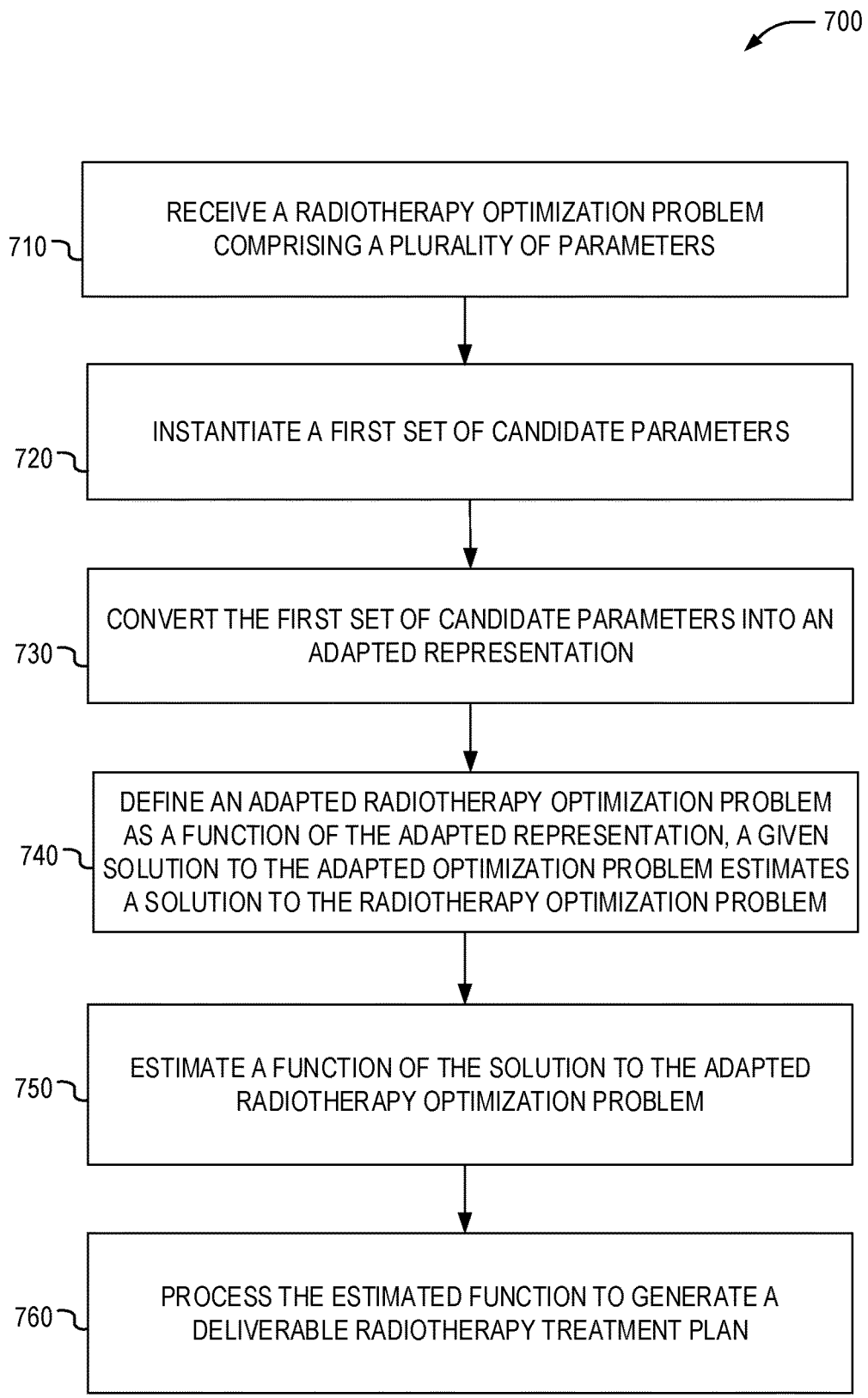
FIG. 7 illustrates a flowchart of exemplary operations for using a machine learning technique to solve a radiotherapy optimization problem, according to some examples of the disclosure.

FIG. 7 is a flowchart illustrating example operations of the treatment processing logic 120 in performing process 700, according to example embodiments. The process 700 may be embodied in computer-readable instructions for execution by one or more processors such that the operations of the process 700 may be performed in part or in whole by the functional components of the treatment processing logic 120; accordingly, the process 700 is described below by way of example with reference thereto. However, in other embodiments, at least some of the operations of the process 700 may be deployed on various other hardware configurations. The process 700 is therefore not intended to be limited to the treatment processing logic 120 and can be implemented in whole, or in part, by any other component. Some or all of the operations of process 700 can be in parallel, out of order, or entirely omitted.

At operation 710, treatment processing logic 120 receives a radiotherapy optimization problem comprising a plurality of parameters.

At operation 720, treatment processing logic 120 processes the radiotherapy optimization problem to instantiate a first set of candidate parameters.

At operation 730, treatment processing logic 120 converts the first set of candidate parameters into an adapted representation.

At operation 740, treatment processing logic 120 defines an adapted radiotherapy optimization problem as a function of the adapted representation such that a given solution to the adapted optimization problem estimates a solution to the radiotherapy optimization problem.

At operation 750, treatment processing logic 120 processes the adapted radiotherapy optimization problem to estimate a function of the solution to the adapted radiotherapy optimization problem.

At operation 760, treatment processing logic 120 processes the estimated function of the solution to the adapted optimization problem to generate a deliverable radiotherapy treatment plan.

As previously discussed, respective electronic computing systems or devices may implement one or more of the methods or functional operations as discussed herein. In one or more embodiments, the radiotherapy processing computing system 110 may be configured, adapted, or used to control or operate the image-guided radiation therapy device 232, perform or implement training or prediction operations, perform or implement the operations of the flowchart for process 700, or perform any one or more of the other methodologies discussed herein (e.g., as part of treatment processing logic 120). In various embodiments, such electronic computing systems or devices operate as a standalone device or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine-readable medium. While the machine-readable medium may have been described in various examples with reference to be a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present disclosure, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present disclosure also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other beneficial results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matters contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, which when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials, and example parameters, functions, and implementations described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled.

What is claimed is:

1. A method for generating a radiotherapy treatment plan, the method comprising:
    receiving, by processor circuitry, a radiotherapy optimization problem, the radiotherapy optimization problem comprising a plurality of parameters;
    processing the radiotherapy optimization problem to instantiate a first set of candidate parameters;
    converting the first set of candidate parameters into an adapted representation;
    defining an adapted radiotherapy optimization problem as a function of the adapted representation such that a given solution to the adapted radiotherapy optimization problem estimates a solution to the radiotherapy optimization problem;
    receiving, by a machine learning model, the adapted radiotherapy optimization problem and processing, by the machine learning model, the received adapted radiotherapy optimization problem to estimate a function of the solution to the adapted radiotherapy optimization problem, the machine learning model comprising a deep neural network, a convolutional neural network or a graph neural network, the machine learning model trained by performing training operations comprising:
    accessing training data; and
    applying the machine learning model to the training data to approximate a mapping between one or more training optimization variables and training parameters of a plurality of training radiotherapy treatment plan optimization problems by minimizing an average error over the training data and adjusting parameters of the machine learning model based on the average error; and
    processing the estimated function of the solution to the adapted radiotherapy optimization problem to generate a deliverable radiotherapy treatment plan, the radiotherapy optimization problem being defined as:

$$x^*(w_S, \hat{d}_S) = \underset{x \in \Omega}{\operatorname{argmin}} g(x) + \sum_{S \in M} w_S \sum_{v \in S} f_S(\varphi_v^T x - \hat{d}_S)$$

where $x^* \in \Omega$ is a solution of the radiotherapy optimization problem, $\Omega$ is a feasible set, $w_S$ is a vector of weights for each structure S, $\varphi_v^T$ is a linear map of x to dose in a voxel v, $\hat{d}_S$ is a reference dose for structure S, and g(x) and $f_S(x)$ are real-valued functions.

2. The method of claim 1, wherein instantiating the first set of candidate parameters comprises a sampling process that generates candidate parameters according to at least one of a deterministic pattern and a probability distribution.

3. The method of claim 1, wherein the machine learning model comprises a first machine learning model of a plurality of machine learning models, and wherein the function of the solution is a first function of the solution, further comprising:
    receiving, in parallel with the first machine learning model, the adapted radiotherapy optimization problem by a second machine learning model of the plurality of machine learning models and processing the received adapted radiotherapy optimization problem by the second machine learning model to generate a second function of the solution to the adapted radiotherapy optimization problem in parallel with generation of the first function of the solution.

4. The method of claim 1, further comprising:
processing at least one of the radiotherapy optimization problem, previously generated candidate parameters and the function of the solution to the adapted radiotherapy optimization problem to generate a new set of candidate parameters.

5. The method of claim 4, wherein the new set of candidate parameters are generated according to a parameter search optimization problem comprising a bilevel optimization problem.

6. The method of claim 5, wherein the parameter search optimization problem is solved using a learned or non-learned optimization process including at least one of a machine learning model, a simplex method, an interior point method, a Newton method, a quasi-Newton method, a Gauss-Newton method, a Levenberg-Marquardt method, a linear least-squares method, a gradient descent method, a projected gradient method, a conjugate gradient method, an augmented Lagrangian method, a Nelder-Mead method, a branch and bound method, a cutting plane method, simulated annealing, or sequential quadratic programming.

7. The method of claim 1, further comprising:
performing a first iteration of solving the radiotherapy optimization problem to generate the first set of candidate parameters;
after processing the received adapted radiotherapy optimization problem to estimate the function of the solution by the machine learning model, converting the function of the solution back to a form suitable for processing by the radiotherapy optimization problem; and
performing a second iteration of solving the radiotherapy optimization problem using the function of the solution, estimated by the machine learning model, to generate a solution to the radiotherapy optimization problem to generate the deliverable radiotherapy treatment plan.

8. The method of claim 1, wherein the processing of the adapted radiotherapy optimization problem to estimate the function of the solution to the adapted radiotherapy optimization problem comprises at least one of a (i) a surrogate function, (ii) upper and lower bounds, (iii) an optimization solver halted before convergence, (iv) interpolation of already obtained results, or (v) a trained machine learning model.

9. The method of claim 1, wherein the function of the solution to the adapted optimization problem comprises at least one of (i) the solution itself, (ii) a resulting dose distribution or dose-based metrics such as dose volume histogram (DVH) criteria, (iii) radiobiological effects, (iv) radiosurgical metrics such as coverage, selectivity or gradient index, (v) metrics quantifying a complexity of radiotherapy delivery, (vi) geometrical deviations, or (vii) sensitivity to uncertainties.

10. The method of claim 1, further comprising at least one of:
assessing whether the estimated solution is tentatively acceptable;
verifying whether the estimated solution is deliverable; or
processing the estimated solution to generate a deliverable solution.

11. The method of claim 10, wherein processing the estimated solution to generate a deliverable solution comprises solving the radiotherapy optimization problem exactly using a corresponding set of candidate parameters.

12. The method of claim 1, further comprising:
converting the function of the solution to the adapted radiotherapy optimization problem from a multi-dimensional tensor to a set of scalars.

13. The method of claim 1, wherein the radiotherapy optimization problem comprises at least one of images of a patient or patient volume, a segmentation of the patient volume, a dose kernel, a dose volume histogram constraint, or a dose constraint.

14. The method of claim 1, wherein the first set of candidate parameters are converted into an adapted representation based on an affine function.

15. The method of claim 1, wherein converting the first set of candidate parameters into an adapted representation comprises mapping organ-specific parameters to voxel-specific parameters structured in a multi-dimensional grid corresponding to a patient geometry.

16. The method of claim 1, wherein the first set of candidate parameters comprise weights and reference doses for each structure in a set of structures, further comprising converting the first set of candidate parameters into a tensor representation by mapping the weights and reference doses to a tensor defined on a voxel grid and concatenating the tensor with dose maps defined on a same voxel grid.

17. The method of claim 1, wherein processing the adapted radiotherapy optimization problem to estimate the function of the solution to the adapted radiotherapy optimization problem is performed in parallel or asynchronously.

18. The method of claim 1, wherein the plurality of parameters are processed based on user input or automatically using an open-loop or closed-loop process.

19. A computing apparatus, the computing apparatus comprising:
at least one processor; and
a memory storing instructions that, when executed by the at least one processor, configure the apparatus to:
receive a radiotherapy optimization problem, the radiotherapy problem comprising a plurality of parameters;
process the radiotherapy optimization problem to instantiate a first set of candidate parameters;
convert the first set of candidate parameters into an adapted representation;
define an adapted radiotherapy optimization problem as a function of the adapted representation such that a given solution to the adapted radiotherapy optimization problem estimates a solution to the radiotherapy optimization problem;
receive, by a machine learning model, the adapted radiotherapy optimization problem and processes, by the machine learning model, the received adapted radiotherapy optimization problem to estimate a function of the solution to the adapted radiotherapy optimization problem, the machine learning model comprising a deep neural network, a convolutional neural network or a graph neural network, the machine learning model trained by performing training operations comprising:
accessing training data; and
applying the machine learning model to the training data to approximate a mapping between one or more training optimization variables and training parameters of a plurality of training radiotherapy treatment plan optimization problems by minimizing an average error over the training data and adjusting parameters of the machine learning model based on the average error; and
processing the estimated function of the solution to the adapted radiotherapy optimization problem to generate a deliverable radiotherapy treatment plan, the radiotherapy optimization problem being defined as:

$$x^*(w_S, \hat{d}_S) = \underset{x \in \Omega}{\operatorname{argmin}} g(x) + \sum_{S \in M} w_S \sum_{v \in S} f_S(\varphi_v^T x - \hat{d}_S)$$

where $x^* \in \Omega$ is a solution of the radiotherapy optimization problem, $\Omega$ is a feasible set, $w_S$ is a vector of weights for each structure S, $\varphi_v^T$, is a linear map of x to dose in a voxel v, $\hat{d}_S$ is a reference dose for structure S, and g (x) and $f_S(x)$ are real-valued functions.

20. The computing apparatus of claim 19, wherein instantiating the first set of candidate parameters comprises a sampling process that generates candidate parameters according to at least one of a deterministic pattern and a probability distribution.

21. The computing apparatus of claim 20, wherein the sampling process is adapted based on at least one of user input or the radiotherapy optimization problem.

22. The computing apparatus of claim 19, wherein the instructions further configure the apparatus to
process at least one of the radiotherapy optimization problem, previously generated candidate parameters and the function of the solution to the adapted radiotherapy optimization problem to generate a new set of candidate parameters.

23. The computing apparatus of claim 22, wherein the new set of candidate parameters are generated according to a parameter search optimization problem comprising a bilevel optimization problem.

24. The computing apparatus of claim 23, wherein the parameter search optimization problem is solved using a learned or non-learned optimization process including at least one of a machine learning model, a simplex method, an interior point method, a Newton method, a quasi-Newton method, a Gauss-Newton method, a Levenberg-Marquardt method, a linear least-squares method, a gradient descent method, a projected gradient method, a conjugate gradient method, an augmented Lagrangian method, a Nelder-Mead method, a branch and bound method, a cutting plane method, simulated anneal, or sequential quadratic programming.

25. The computing apparatus of claim 19, wherein the adapted representation is at least one of a tensor representation, a canonical form of the radiotherapy optimization problem, or a representation of the radiotherapy optimization problem by an algebraic modeling language.

26. The computing apparatus of claim 19, wherein the processing of the adapted radiotherapy optimization problem to estimate the function of the solution to the adapted radiotherapy optimization problem comprises at least one of a (i) a surrogate function, (ii) upper and lower bounds, (iii) an optimization solver halted before convergence, (iv) interpolation of already obtained results, or (v) a trained machine learning model.

27. The computing apparatus of claim 19, wherein the function of the solution to the adapted optimization problem comprises at least one of (i) the solution itself, (ii) a resulting dose distribution or dose-based metrics such as dose volume histogram (DVH) criteria, (iii) radiobiological effects, (iv) radiosurgical metrics such as coverage, selectivity or gradient index, (v) metrics quantifying a complexity of radiotherapy delivery, (vi) geometrical deviations, or (vii) sensitivity to uncertainties.

28. The computing apparatus of claim 19, wherein the instructions further configure the apparatus to at least one of:
assess whether the estimated solution is tentatively acceptable;
verify whether the estimated solution is deliverable; or
processing the estimated solution to generate a deliverable solution.

29. The computing apparatus of claim 28, wherein processing the estimated solution to generate a deliverable solution comprises solving the radiotherapy optimization problem exactly using a corresponding set of candidate parameters.

30. The computing apparatus of claim 19, wherein the instructions further configure the apparatus to:
convert the function of the solution to the adapted radiotherapy optimization problem from a multi-dimensional tensor to a set of scalars.

31. The computing apparatus of claim 19, wherein the radiotherapy optimization problem comprises at least one of images of a patient or patient volume, a segmentation of the patient volume, a dose kernel, a dose volume histogram constraint, or a dose constraint.

32. The computing apparatus of claim 19, wherein the first set of candidate parameters are converted into an adapted representation based on an affine function.

33. The computing apparatus of claim 19, wherein converting the first set of candidate parameters into an adapted representation comprises mapping organ-specific parameters to voxel-specific parameters structured in a multi-dimensional grid corresponding to a patient geometry.

34. The computing apparatus of claim 19, wherein the first set of candidate parameters comprise weights and reference doses for each structure in a set of structures, wherein the instructions further configure the apparatus to convert the first set of candidate parameters into a tensor representation by mapping the weights and reference doses to a tensor defined on a voxel grid and concatenating the tensor with dose maps defined on a same voxel grid.

35. The computing apparatus of claim 19, wherein processing the adapted radiotherapy optimization problem to estimate the function of the solution to the adapted radiotherapy optimization problem is performed in parallel or asynchronously.

36. The computing apparatus of claim 19, wherein the plurality of parameters are processed based on user input or automatically use an open-loop or closed-loop process.

37. A non-transitory computer-readable storage medium, the computer-readable storage medium including instructions that when executed by a computer, cause the computer to:
receive a radiotherapy optimization problem, the radiotherapy optimization problem comprising a plurality of parameters;
process the radiotherapy optimization problem to instantiate a first set of candidate parameters;
convert the first set of candidate parameters into an adapted representation;
define an adapted radiotherapy optimization problem as a function of the adapted representation such that a given solution to the adapted radiotherapy optimization problem estimates a solution to the radiotherapy optimization problem;
receiving, by a machine learning model, the adapted radiotherapy optimization problem and processing, by the machine learning model, the received adapted radiotherapy optimization problem to estimate a function of the solution to the adapted radiotherapy optimization problem, the machine learning model comprising a deep neural network, a convolutional neural network or a graph neural network, the machine learning model trained by performing training operations comprising:

accessing training data; and applying the machine learning model to the training data to approximate a mapping between one or more training optimization variables and training parameters of a plurality of training radiotherapy treatment plan optimization problems by minimizing an average error over the training data and adjusting parameters of the machine learning model based on the average error; and processing the estimated function of the solution to the adapted radiotherapy optimization problem to generate a deliverable radiotherapy treatment plan, the radiotherapy optimization problem being defined as:

$$x^*(w_S, \hat{d}_S) = \underset{x \in \Omega}{\operatorname{argmin}}\ g(x) + \sum_{S \in \mathcal{M}} w_S \sum_{v \in S} f_S(\varphi_v^T x - \hat{d}_S)$$

where $x^* \in \Omega$ is a solution of the radiotherapy optimization problem, $\Omega$ is a feasible set, $w_S$ is a vector of weights for each structure S, $\varphi_v^T$ is a linear map of x to dose in a voxel v, $\hat{d}_S$ is a reference dose for structure S, and $g(x)$ and $f_S(x)$ are real-valued functions.

* * * * *